(12) United States Patent
Tsuji

(10) Patent No.: US 10,809,521 B2
(45) Date of Patent: Oct. 20, 2020

(54) ENDOSCOPE OBJECTIVE OPTICAL SYSTEM

(71) Applicant: OLYMPUS CORPORATION, Hachioji-shi, Tokyo (JP)

(72) Inventor: Yoshifumi Tsuji, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 79 days.

(21) Appl. No.: 16/171,021

(22) Filed: Oct. 25, 2018

(65) Prior Publication Data

US 2019/0064500 A1 Feb. 28, 2019

Related U.S. Application Data

(63) Continuation of application No. PCT/JP2017/020692, filed on Jun. 2, 2017.

(30) Foreign Application Priority Data

Sep. 1, 2016 (JP) .................................. 2016-170750

(51) Int. Cl.
*G02B 23/24* (2006.01)
*G02B 13/04* (2006.01)
(Continued)

(52) U.S. Cl.
CPC ........ *G02B 23/243* (2013.01); *A61B 1/00096* (2013.01); *A61B 1/00188* (2013.01); *G02B 13/04* (2013.01); *G02B 15/177* (2013.01)

(58) Field of Classification Search
CPC .... G02B 23/243; G02B 13/04; G02B 15/177; A61B 1/00096; A61B 1/00188
(Continued)

(56) References Cited

U.S. PATENT DOCUMENTS

| 5,916,148 A | 6/1999 | Tsuyuki |
| 6,206,825 B1 | 3/2001 | Tsuyuki |
| (Continued) | | |

FOREIGN PATENT DOCUMENTS

| JP | 09010170 A | 1/1997 |
| JP | 2006084886 A | 3/2006 |
| (Continued) | | |

OTHER PUBLICATIONS

International Search Report (ISR) dated Aug. 29, 2017 issued in International Application No. PCT/JP2017/020692.
(Continued)

*Primary Examiner* — James R Greece
(74) *Attorney, Agent, or Firm* — Holtz, Holtz & Volek PC

(57) ABSTRACT

An endoscope objective optical system consists of a front group having a negative refractive power, an aperture stop, and a rear group having a positive refractive power. The front group consists of a first lens having a negative refractive power, and a second lens having a positive refractive power, and the rear group consists of a third lens having a positive refractive power, a cemented lens of a fourth lens having a positive refractive power and a fifth lens having a negative refractive power, and a sixth lens having a positive refractive power. An object-side surface of the first lens is a flat surface, and the second lens has a meniscus shape with a convex surface directed toward an image side, and the sixth lens is cemented to an image pickup element, and the following conditional expression (1) is satisfied:

$$-1.2 \leq D6/F12 \leq -0.47 \qquad (1).$$

10 Claims, 13 Drawing Sheets

(51) Int. Cl.
*A61B 1/00* (2006.01)
*G02B 15/177* (2006.01)

(58) Field of Classification Search
USPC .......................................................... 359/752
See application file for complete search history.

(56) References Cited

U.S. PATENT DOCUMENTS

| | | | |
|---|---|---|---|
| 9,568,725 B2* | 2/2017 | Ushio | G02B 13/04 |
| 2006/0061880 A1 | 3/2006 | Kawakami | |
| 2012/0127598 A1* | 5/2012 | Katahira | G02B 9/60 |
| | | | 359/770 |
| 2012/0147164 A1 | 6/2012 | Sasamoto | |
| 2016/0306162 A1* | 10/2016 | Ushio | G02B 13/04 |

FOREIGN PATENT DOCUMENTS

| | | |
|---|---|---|
| JP | 2008107478 A | 5/2008 |
| JP | 4997348 B2 | 8/2012 |
| JP | 5927368 B1 | 6/2016 |
| WO | 2011125539 A1 | 10/2011 |
| WO | 2016031586 A1 | 3/2016 |

OTHER PUBLICATIONS

Written Opinion dated Aug. 29, 2017 issued in International Application No. PCT/JP2017/020692.

International Preliminary Report on Patentability (IPRP) (and English language translation thereof) and Written Opinion dated Mar. 5, 2019 issued in counterpart International Application No. PCT/JP2017/020692.

Chinese Office Action (and English language translation thereof) dated May 8, 2020 issued in Chinese Application No. 201780026828.6.

* cited by examiner

ENDOSCOPE OBJECTIVE OPTICAL SYSTEM

CROSS-REFERENCE TO RELATED APPLICATION

The present application is a continuation application of PCT/JP2017/020692 filed on Jun. 2, 2017 which is based upon and claims the benefit of priority from Japanese Patent Application No. 2016-170750 filed on Sep. 1, 2016; the entire contents of which are incorporated herein by reference.

BACKGROUND OF THE INVENTION

Field of the Invention

The present invention relates to a small-size and bright objective optical system, and particularly, to an endoscope objective optical system.

Description of the Related Art

Endoscope is an instrument that has been used widely in a medical field and an industrial field. Particularly, in the medical field, from a viewpoint of reducing stress on a patient and improving an accuracy of diagnosis, small-sizing and making the number of pixels large of an image pickup element such as a CCD (charge coupled device) and CMOS (complementary metal-oxide semiconductor) of an endoscope has been progressing, and a pixel pitch has been becoming smaller year by year. Therefore, even for an endoscope objective optical system, facilitating small-sizing while satisfying an optical performance such as widening an angle of view and an aberration correction, has been sought. Small-size endoscope objective optical systems have been proposed in Japanese Patent Publication No. 4997348 and Japanese Patent Publication No. 5927368. Moreover, small-size optical systems for digital cameras have been proposed in Japanese Patent Application Laid-open Publication No. 2008-107478 and Japanese Patent Application Laid-open Publication No. 2006-84886.

SUMMARY OF THE INVENTION

An endoscope objective optical system according to at least some embodiments of the present invention consists of, in order from an object side, a front group having a negative refractive power as a whole, an aperture stop, and a rear group having a positive refractive power as a whole, wherein the front group consists of a first lens which is a single lens having a negative refractive power, and a second lens which is a single lens having a positive refractive power, in order from the object side, and the rear group consists of a third lens which is a single lens having a positive refractive power, a cemented lens of a fourth lens having a positive refractive power and a fifth lens having a negative refractive power, and a sixth lens having a positive refractive power, and an object-side surface of the first lens is a flat surface, and the second lens has a meniscus shape with a convex surface directed toward an image side, and the sixth lens is cemented to an image pickup element, and the following conditional expression (1) is satisfied:

$$-1.2 \leq D6/F12 \leq -0.47 \quad (1)$$

where,

D6 denotes a thickness of the sixth lens, and

F12 denotes a combined focal length from the first lens up to the second lens.

DETAILED DESCRIPTION OF THE INVENTION

An endoscope objective optical system according to an embodiment will be described below in detail by referring to the accompanying diagrams. However, the present invention is not restricted to the embodiments and the examples described below.

Figure 1:
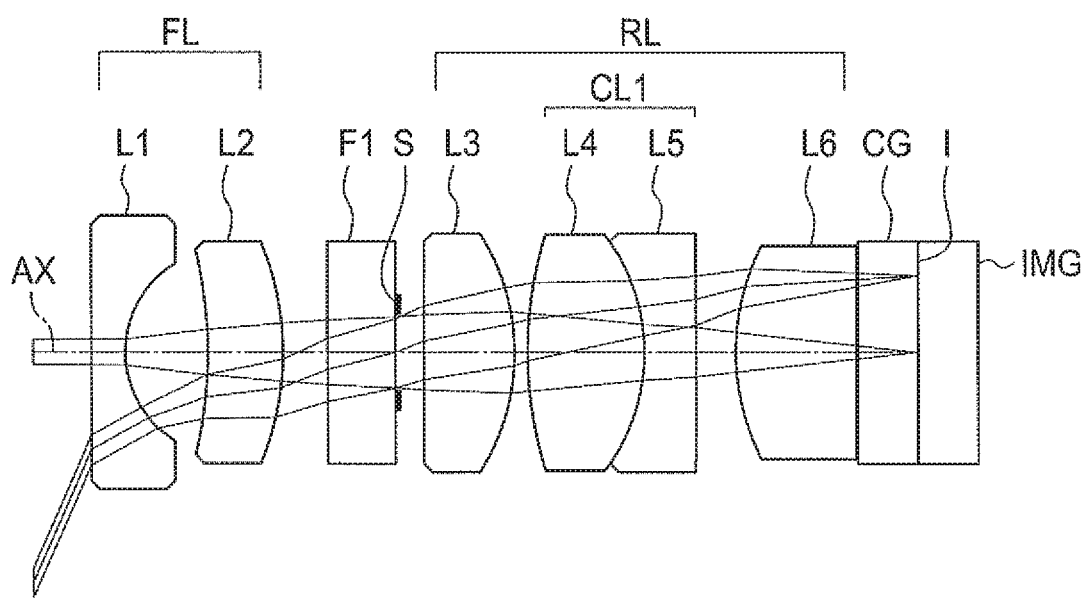
FIG. 1 is a cross-sectional view showing a lens arrangement of an endoscope objective optical system according an embodiment of the present invention.

FIG. 1 is a cross-sectional view showing a lens arrangement of an endoscope objective optical system according to an embodiment of the present invention.

The endoscope objective optical system of the present embodiment consists of, in order from an object side, a front group FL having a negative refractive power as a whole, an aperture stop S, and a rear group RL having a positive refractive power as a whole, wherein the front group FL includes a first lens L1 which is a single lens having a negative refractive power, and a second lens L2 which is a single lens having a positive refractive power, in order from the object side, and the rear group RL includes a third lens L3 which is a single lens having a positive refractive power, a cemented lens CL1 of a fourth lens L4 having a positive refractive power and a fifth lens L5 having a negative refractive power, and a sixth lens L6 having a positive refractive power, and an object-side surface of the first lens L1 is a flat surface, and the second lens L2 has a meniscus shape with a convex surface directed toward an image side, and the sixth lens L6 is cemented to an image pickup element IMG, and the following conditional expression (1) is satisfied:

$$-1.2 \leq D6/F12 \leq -0.47 \quad (1)$$

where,

D6 denotes a thickness of the sixth lens L6, and

F12 denotes a combined focal length from the first lens L1 up to the second lens L2.

Moreover, the aperture stop S is formed on an image-side surface of an infra-red absorption filter F1. Moreover, a cover glass CG for preventing the image pickup element IMG from being scratched is stuck to an image-side surface I of the image pickup element IMG. The sixth lens L6 is cemented to the cover glass CG. Consequently, the sixth lens L6 is cemented to the image pickup element IMG.

Reasons for and effects of adopting such arrangement in the present embodiment will be described below. For arranging a small-size and high-performance endoscope objective optical system that can be used in an endoscope, firstly, the first lens L1 having a negative refractive power, of which a surface nearest to object is a flat surface, is disposed, and on an image side thereof, a second lens L2 having a positive refractive power and having a meniscus shape with a convex surface directed toward the image side, is disposed.

In such manner, a retro-focus arrangement is adopted, and the second lens L2 having a positive refractive power is disposed such that a lens diameter does not become large, while correcting an aberration at the first lens L1. Accordingly, a small-size and high-performance objective optical system suitable for an endoscope is arranged.

Moreover, for the first lens L1, it is preferable to make the following arrangement. In an observation by an endoscope, when a dirt or blood is adhered to a lens surface on the object side of the first lens L1, cleaning of the lens surface is carried out by injecting water from a nozzle provided at a front-end of the endoscope. At the time of cleaning, when a shape of the lens surface on the object side of the first lens L1 is a convex shape, the dirt is hard to be removed. Moreover, when the shape of the lens surface on the object side of the first lens L1 is a concave shape, the water removal is not favorable due to water being accumulated. Furthermore, when the lens surface on the object side of the first lens L1 is convex-shaped, scratching and cracking due to an impact are susceptible to occur. For this reason, the first lens L1 having a negative refractive power is let to be a planoconcave lens, and the first lens L1 having a negative refractive power is disposed such that the flat surface is directed toward the object side. By making such arrangement, the water removal during the observation is made favorable and the cracking of lens due to an impact is reduced.

Moreover, by disposing a positive lens group for holding a positive refractive power contributing mainly to image formation, on the image side of the second lens L2, an occurrence of an aberration is suppressed despite of Fno being made small and bright, and a refractive power distribution necessary for small-sizing is made.

Moreover, a cemented lens of a positive lens and a negative lens is disposed at a position on the image side of the third lens L3, at which a peripheral light-ray height becomes high. According, a chromatic aberration is corrected.

Furthermore, the sixth lens L6 having a positive refractive power which is cemented to the image pickup element IMG is disposed on the image side in the rear group RL. Accordingly, even when an optical magnification is increased, and the focusing position is varied, it is possible to achieve an optical performance with a small effect thereon.

However, as mentioned above, only by making the positive refractive power of the sixth lens L6 large and alleviating the focusing sensitivity, the astigmatism is deteriorated and it is not possible to secure a favorable optical performance. Therefore, it is necessary to make the sixth lens L6 thick, to increase the optical magnification by moving a curved surface of the lens away from an image plane, and to alleviate the focusing sensitivity. Moreover, for small-sizing and suppressing each aberration, it is desirable that the arrangement is made to satisfy the following conditional expression (1):

$$-1.2 \leq D6/F12 \leq -0.47 \quad (1)$$

where,
D6 denotes the thickness of the sixth lens L6, and
F12 denotes the combined focal length from the first lens L1 up to the second lens L2.

Conditional expression (1) is related to a ratio of the thickness of the sixth lens L6 and the combined focal length from the first lens L1 up to the second lens L2.

In a case of exceeding an upper limit value of conditional expression (1), the astigmatism becomes substantial due to weakening of the negative refractive power of the first lens L1 and the second lens L2, and it is not possible to achieve a high definition image quality and a wide visual field. Moreover, the curved surface of the sixth lens L6 becomes close to the image plane, and it is not possible to achieve an adequate focusing alleviation effect. Consequently, the endoscope objective optical system becomes weak to the focusing-position shift due to the manufacturing variability.

In a case of falling below a lower limit value of conditional expression (1), it is possible to achieve an adequate focusing alleviation effect, but the negative refractive power of the first lens L1 and the second lens L2 becomes excessively large, and an aberration such as a coma is deteriorated. Moreover, since, either an overall length of the optical system becomes long due to the curved surface of the sixth lens L6 being moved away from the image plane or a back focus for focusing cannot be secured, it is not possible to achieve a small-size and high definition image quality.

It is more preferable that the following conditional expression (1') be satisfied instead of conditional expression (1).

$$-1.1 \leq D6/F12 \leq -0.5 \quad (1')$$

It is even more preferable that the following conditional expression (1") be satisfied instead of conditional expression (1).

$$-1.0 \leq D6/F12 \leq -0.55 \quad (1'')$$

Moreover, for making an arrangement of the retro-focus type, the first lens L1 having a negative refractive power is required to have a comparatively large negative refractive power. However, as mentioned above, when the negative refractive power of the first lens L1 is made excessively large, aberrations such as the coma may be deteriorated. Moreover, since the fourth lens L4 having a positive refractive power is disposed far from the aperture stop S, light-ray height increases in the fourth lens L4. Therefore, in the fourth lens L4, a balance of the coma of the peripheral performance and each chromatic aberration is kept. Accordingly, by setting appropriately the refractive power of the first lens L1 having a negative refractive power and the fourth lens L4 having a positive refractive power, even in the endoscope objective optical system with a fast Fno, in which the back-focus is secured while the focusing sensitivity being alleviated adequately, it is possible to take an overall aberration balance.

Therefore, according to a preferable aspect of the present embodiment, it is desirable that the following conditional expression (2) is satisfied:

$$1.5 \leq |F4/F1| \leq 2.0 \quad (2)$$

where,
F4 denotes a focal length of the fourth lens L4, and
F1 denotes a focal length of the first lens L1.

Conditional expression (2) is related to a ratio of the focal length of the fourth lens L4 and the focal length of the first lens L1.

In a case of exceeding an upper limit value of conditional expression (2), the negative refractive power becomes excessively large, and the coma, without being corrected thoroughly, is deteriorated, and correction of the chromatic aberration becomes inadequate.

In a case of falling below a lower limit value of conditional expression (2), either a lens diameter becomes excessively large and the small-sizing cannot be fulfilled, or the chromatic aberration is corrected excessively.

It is more preferable that the following conditional expression (2') be satisfied instead of conditional expression (2).

$$1.55 \leq |F4/F1| \leq 1.95 \quad (2')$$

It is even more preferable that the following conditional expression (2") be satisfied instead of conditional expression (2).

$$1.6 \leq |F4/F1| \leq 1.75 \quad (2'')$$

Moreover, since the first lens L1 and the fifth lens L5 being disposed far away from the aperture stop S, there is an effect on optical performance at a peripheral portion of an image field, and since a peripheral light-ray height also becomes high, there is an effect on the lens diameter as well. For cancelling an aberration at the peripheral portion of the image field, an arrangement of the fifth lens L5 having a negative refractive power at which the peripheral light-ray height becomes high, becomes significant.

Therefore, according to a preferable aspect of the present embodiment, it is desirable that the following conditional expression (3) is satisfied:

$$1.6 \leq |F5/F1| \leq 2.0 \quad (3)$$

where,
F5 denotes a focal length of the fifth lens L5, and
F1 denotes the focal length of the first lens L1.

In a case of exceeding an upper limit value of conditional expression (3), the negative refractive power becomes excessively large, and either the coma, not being corrected thoroughly, is deteriorated, or correction of a chromatic aberration of magnification becomes inadequate.

In a case of falling below a lower limit value of conditional expression (3), either a lens diameter becomes excessively large or correction of the chromatic aberration of magnification becomes excessive.

It is more preferable that the following conditional expression (3') be satisfied instead of conditional expression (3).

$$1.63 \leq |F5/F1| \leq 1.95 \quad (3')$$

It is even more preferable that the following conditional expression (1") be satisfied instead of conditional expression (3).

$$1.66 \leq |F5/F1| \leq 1.8 \quad (3'')$$

Moreover, in an objective optical system with a fast Fno, correction of a spherical aberration and the coma tend to be disadvantageous. The positive refractive power which is major in the lens arrangement of the present embodiment is secured by the third lens L3, and the fourth lens L4 in the cemented lens CL1. Therefore, an aberration is susceptible to occur at these lenses. Moreover, the positive refractive power forming the retro-focus arrangement is also held by the third lens L3 and the fourth lens L4, and has a relationship with the size of the objective optical system. Particularly, since a height of an axial light ray becomes high, an aberrational effect is high, and moreover, it is easy to secure the refractive power by the third lens L3 which is not cemented, and contribution to securing the back focus at the time of focusing alleviation is also high. Therefore, it is necessary to set appropriately the refractive power of the third lens L3 and the fourth lens L4.

Therefore, according to a preferable aspect of the present embodiment, it is desirable that the following conditional expression (4) is satisfied:

$$0.16 \leq |(R3R+R4L)/(R3R-R4L)| \leq 0.5 \qquad (4)$$

where,

R3R denotes a radius of curvature of an image side of the third lens L3, and

R4L denotes a radius of curvature of an object side of the fourth lens L4.

Conditional expression (4) is regarding an appropriate relationship of the radius of curvature of the image side of the third lens L3 and the radius of curvature of the object side of the fourth lens L4.

In a case of exceeding an upper limit value of conditional expression (4), since correction of the coma is degraded, and the overall length also becomes long, it is not possible to achieve a small-size and high definition image quality.

In a case of falling below a lower limit value of conditional expression (4), the spherical aberration is deteriorated, and it is not possible to secure back focus which is necessary for focusing.

It is more preferable that the following conditional expression (4') be satisfied instead of conditional expression (4).

$$0.17 \leq |(R3R+R4L)/(R3R-R4L)| \leq 0.45 \qquad (4')$$

It is even more preferable that the following conditional expression (4") be satisfied instead of conditional expression (4).

$$0.2 \leq |(R3R+R4L)/(R3R-R4L)| \leq 0.4 \qquad (4")$$

Moreover, the first lens L1 having a negative refractive power and the second lens L2 having a positive refractive power disposed in the front group FL play a significant role in widening the angle of view and small-sizing of the optical system. In this case, the radius of curvature of the second lens L2 having a positive refractive power contributes to occurrence of the coma and the chromatic aberration. Moreover, although the radius of curvature of the sixth lens L6 plays a significant role in alleviating the focusing sensitivity, it contributes to an occurrence of astigmatism.

Therefore, according to a preferable aspect of the present embodiment, it is desirable that the following conditional expressions (5) and (6) are satisfied for taking a balance of an amount of each aberration that occurs, the lens diameter and the focusing sensitivity. Preferably, it is desirable that conditional expressions (5) and (6) are satisfied simultaneously:

$$--2.0 \leq F12/R6L \leq -0.62 \qquad (5), \text{ and}$$

$$-4.0 \leq R2L/R6L \leq -1.5 \qquad (6)$$

where,

F12 denotes the combined focal length from the first lens up to the second lens L2, R6L denotes a radius of curvature of an object side of the sixth lens L6, and R2L denotes a radius of curvature of an object side of the second lens L2.

Conditional expression (5) is related to a ratio of the combined focal length from the first lens L1 up to the second lens L2, and the radius of curvature of the object side of the sixth lens L6. Conditional expression (6) is related to a ratio of the radius of curvature of the second lens L2 and the radius of curvature of the sixth lens L6.

In a case of exceeding an upper limit value of conditional expression (5), either the coma is deteriorated or the astigmatism is deteriorated.

In a case of falling below a lower limit value of conditional expression (5), since either the lens diameter becomes large or an adequate focusing alleviation effect cannot be achieved, endoscope objective optical system becomes weak to a shift in focusing position due to the manufacturing variability.

In a case of exceeding an upper limit value of conditional expression (6), either the chromatic aberration is deteriorated or the astigmatism is deteriorated.

In a case of falling below a lower limit value of conditional expression (6), since either the coma is deteriorated or an adequate focusing alleviation effect cannot be achieved, the endoscope objective optical system becomes weak to the shift in focusing position due to the manufacturing variability.

It is more preferable that the following conditional expressions (5') and (6') be satisfied instead of conditional expressions (5) and (6).

$$-1.8 \leq F12/R6L \leq -0.7 \qquad (5')$$

$$-3.8 \leq R2L/R6L \leq -1.6 \qquad (6')$$

It is even more preferable that the following conditional expressions (5") and (6") be satisfied instead of conditional expressions (5) and (6).

$$-1.6 \leq F12/R6L \leq -0.75 \qquad (5")$$

$$-3.5 \leq R2L/R6L \leq -1.7 \qquad (6")$$

The light-ray height being high at a surface on the image side of the fourth lens L4, it contributes largely to correction of each chromatic aberration. Moreover, at a surface on the image side of the third lens L3, since an amount of the coma that occurs and a height of an axial light ray become high, it contributes to the spherical aberration as well.

Therefore, according to a preferable aspect of the present embodiment, it is desirable that the following conditional expression (7) be satisfied for correction of each chromatic aberration and each aberration:

$$0.55 \leq R4R/R3R \leq 1.2 \qquad (7)$$

where,

R4R denotes a radius of curvature of an image side of the fourth lens L4, and

R3R denotes the radius of curvature of an image side of the third lens L3.

Conditional expression (7) is related to a ratio of the radius of curvature of the image side of the fourth lens L4 and the radius of curvature of the image side of the third lens L3.

In a case of exceeding an upper limit value of conditional expression (7), either correction of the chromatic aberration becomes inadequate or the spherical aberration is deteriorated, and also it is not possible to secure the back focus necessary for focusing.

In a case of falling below a lower limit value of conditional expression (7), since either correction of the chromatic aberration becomes excessive or the coma is deteriorated, and the overall length of the optical system becomes long, it is not possible to achieve a small-size and high definition image quality.

It is more preferable that the following conditional expression (7') be satisfied instead of conditional expression (7).

$$0.65 \leq R4R/R3R \leq 1.15 \quad (7')$$

It is even more preferable that the following conditional expression (7") be satisfied instead of conditional expression (7).

$$0.7 \leq R4R/R3R \leq 1.1 \quad (7'')$$

Moreover, according to a preferable aspect of the present embodiment, it is desirable that the following conditional expression (8) be satisfied:

$$0.6 \leq R4R/R2R \leq 1.0 \quad (8)$$

where,
R4R denotes the radius of curvature of an image side of the fourth lens L4, and
R2R denotes a radius of curvature of an image side of the second lens L2.

Conditional expression (8) is related to a ratio of the radius of curvature of the image side of the fourth lens L4 and the radius of curvature of the image side of the second lens L2.

In the endoscope which is small-size and is suitable for an image pickup element with a large number of pixels, correction of the chromatic aberration is significant. Conditional expression (8) is related to the chromatic aberration as conditional expression (7), and a surface on the image side of the second lens L2 contributes substantially to each chromatic aberration.

In a case of exceeding an upper limit value of conditional expression (8), either correction of the chromatic aberration of magnification becomes inadequate or correction of a longitudinal chromatic aberration becomes inadequate, and it is also not possible to secure the back focus which is necessary for focusing.

In a case of falling below a lower limit value of conditional expression (8), since either correction of the chromatic aberration of magnification becomes excessive or correction of the longitudinal chromatic aberration becomes excessive, and the overall length of the optical system becomes long, it is not possible to achieve a small-size and high definition image quality.

It is more preferable that the following conditional expression (8') be satisfied instead of conditional expression (8).

$$0.62 \leq R4R/R2R \leq 0.9 \quad (8')$$

It is even more preferable that the following conditional expression (8") be satisfied instead of conditional expression (8).

$$0.65 \leq R4R/R2R \leq 0.7 \quad (8'')$$

Moreover, for making the retro-focus arrangement, the third lens L3 having a positive refractive power has a comparatively large refractive power. Consequently, an amount of aberration that occurs also becomes large.

Therefore, according to a preferable aspect of the present embodiment, it is desirable that the following conditional expression (9) is satisfied:

$$0.5 \leq |(R3L+R3R)/(R3L-R3R)| \leq 5 \quad (9)$$

where,
R3R denotes the radius of curvature of an image side of the third lens L3, and
R3L denotes a radius of curvature of an object side of the third lens L3.

Conditional expression (9) is related to a ratio of the radius of curvature of the image side of the third lens L3 and the radius of curvature of the object side of the third lens L3.

In a case of exceeding an upper limit value of conditional expression (9), the coma is deteriorated, and also the overall length of the optical system becomes long.

In a case of falling below a lower limit value of conditional expression (9), correction of the chromatic aberration of magnification becomes inadequate, and also it is not possible to secure the back focus necessary for focusing.

It is more preferable that the following conditional expression (9') be satisfied instead of conditional expression (9).

$$0.7 \leq |(R3L+R3R)/(R3L-R3R)| \leq 4 \quad (9')$$

It is even more preferable that the following conditional expression (9") be satisfied instead of conditional expression (9).

$$0.8 \leq |(R3L+R3R)/(R3L-R3R)| \leq 3.5 \quad (9'')$$

The cemented lens CL1 of the fourth lens L4 and the fifth lens L5 contributes largely to correction of each chromatic aberration, and the positive refractive power of the sixth lens L6 contributes largely to alleviation of the focusing sensitivity.

Therefore, for fulfilling alleviation of the focusing sensitivity while correcting the chromatic aberration, according to a preferable aspect of the present embodiment, it is desirable that the following conditional expression (10) be satisfied:

$$2.3 \leq F45/F6 \leq 7.3 \quad (10)$$

where,
F45 denotes a focal length of the cemented lens of the fourth lens L4 and the fifth lens L5, and
F6 denotes a focal length of the sixth lens L6.

In a case of exceeding an upper limit value of conditional expression (10), either correction of the chromatic aberration of magnification becomes excessive or the astigmatism is deteriorated.

In a case of falling below a lower limit value of conditional expression (10), since either the chromatic aberration of magnification becomes inadequate or it is not possible to achieve an adequate focusing alleviation effect, the endoscope objective optical system becomes weak to the focusing-position shift due to the manufacturing variability.

It is more preferable that the following conditional expression (10') be satisfied instead of conditional expression (10).

$$2.5 \leq F45/F6 \leq 7.2 \quad (10')$$

It is even more preferable that the following conditional expression (10") be satisfied instead of conditional expression (10).

$$2.7 \leq F45/F6 \leq 7.1 \quad (10'')$$

Each example of the present invention will be described below.

EXAMPLE 1

Figure 2A:
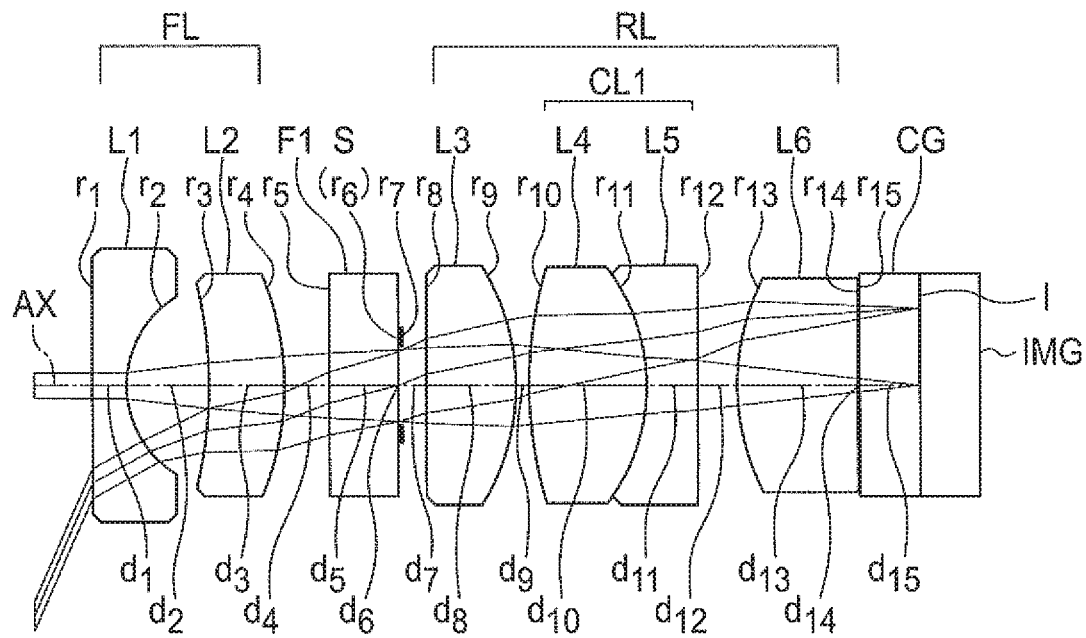
FIG. 2A is a cross-sectional view showing a lens arrangement of an endoscope objective optical system according to an example 1 of the present invention.
Figures 2B, 2C, 2D, 2E:
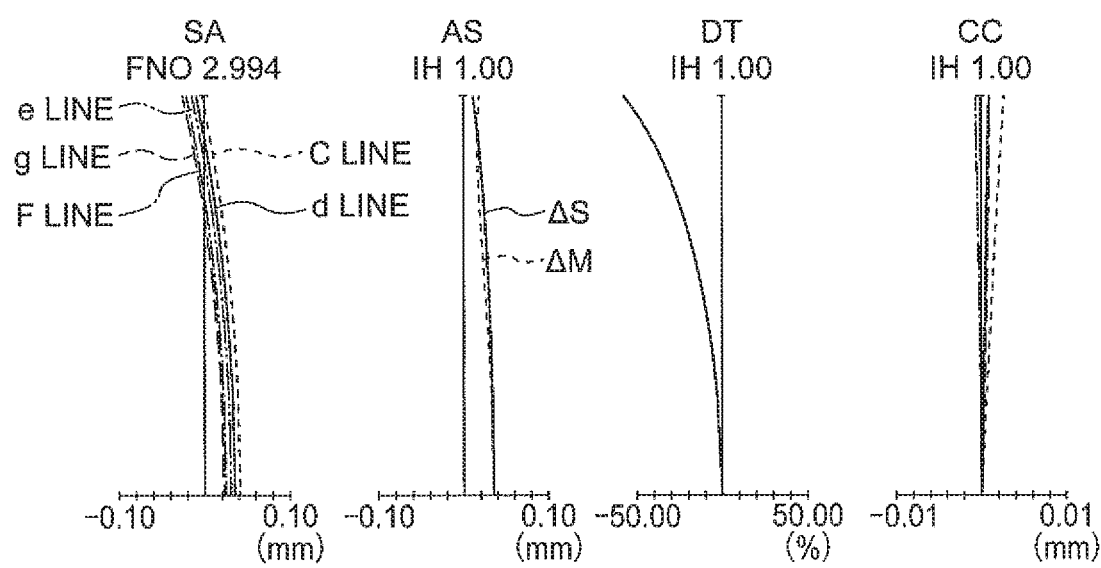
FIG. 2B, FIG. 2C, FIG. 2D, and FIG. 2E are aberration diagrams showing a spherical aberration (SA), an astigmatism (AS), a distortion (DT), and a chromatic aberration of magnification (CC) respectively, of the example 1.

An endoscope objective optical system according to an example 1 will be described below. FIG. 2A is a cross-sectional view showing a lens arrangement of the endoscope objective optical system according to the present example.

In the present example, the endoscope objective optical system includes in order from an object side, a front group FL having a negative refractive power as a whole, an aperture stop S, and a rear group RL having a positive refractive power as a whole.

The endoscope objective optical system of the present example includes in order from the object side, a first lens L1 which is a planoconcave negative lens having a flat surface directed toward the object side, a second meniscus lens L2 having a positive refractive power and having a convex surface directed toward an image side, an infra-red absorption filter F1, the aperture stop S, a third lens L3 which is a biconvex positive lens, a fourth lens L4 which is a biconvex positive lens, a fifth meniscus lens L5 having a negative refractive power and having a concave surface directed toward the object side, a sixth lens L6 having a positive refractive power and having a convex surface directed toward the object side, and a CCD cover glass CG. In this example, I denotes an image pickup surface and IMG denotes an image pickup element.

The front group FL includes the first lens L1 having a negative refractive power and the second meniscus lens L2 having a positive refractive power. The rear group RL includes the third lens L3 having a positive refractive power, the fourth lens L4 having a positive refractive power, the fifth meniscus lens L5 having a negative refractive power, and the sixth lens L6 having a positive refractive power.

Moreover, a YAG (yttrium aluminum garnet) laser cut coating is applied to an object side of the infra-red absorption filter F1, and an LD laser cut coating is applied to an image side of the infra-red absorption filter F1.

The fourth lens L4 having a positive refractive power and the fifth meniscus lens L5 having a negative refractive power are cemented and form a cemented lens CL1. The sixth lens L6 having a positive refractive power and the CCD cover glass CG are cemented.

FIG. 2B, FIG. 2C, FIG. 2D, and FIG. 2E are aberration diagrams showing a spherical aberration (AS), an astigmatism (AS), a distortion (DT), and a chromatic aberration of magnification (CC) respectively, of the example 1.

EXAMPLE 2

Figure 3A:
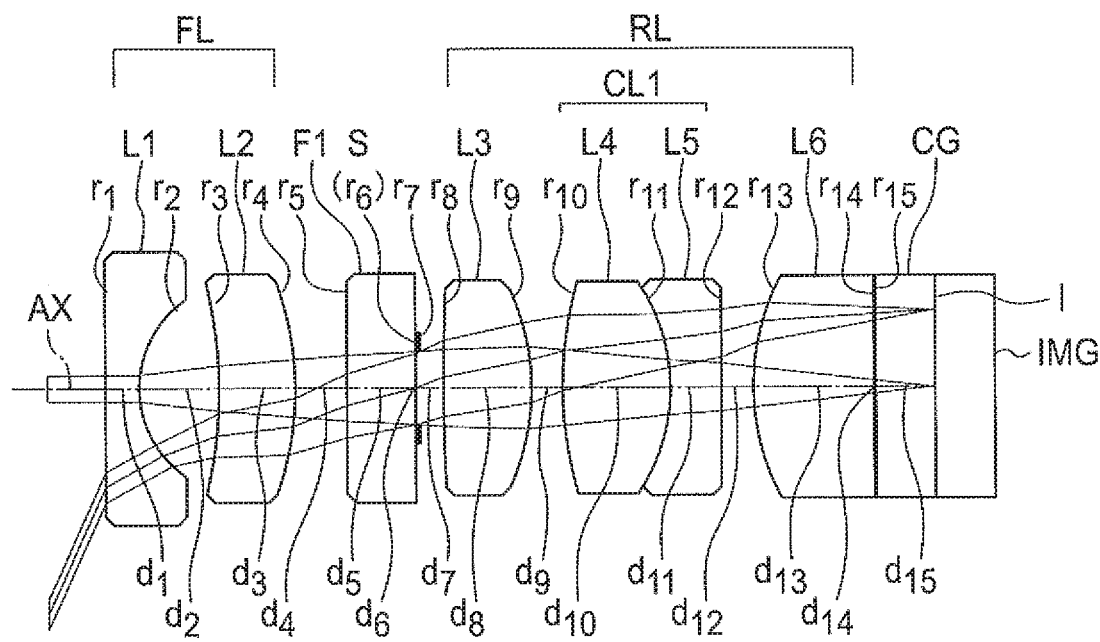
FIG. 3A is a cross-sectional view showing a lens arrangement of an endoscope objective optical system according to an example 2 of the present invention.
Figures 3B, 3C, 3D, 3E:
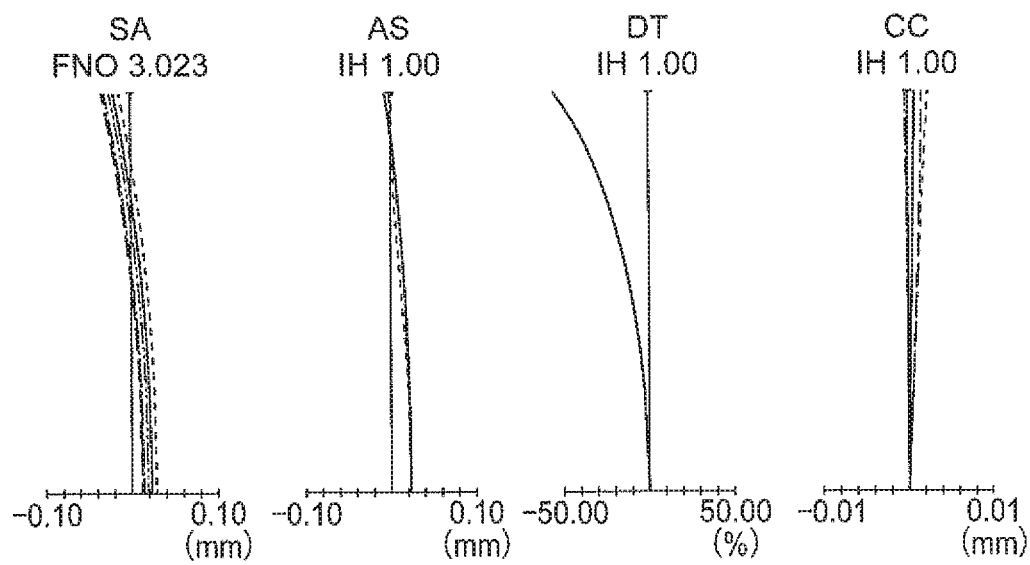
FIG. 3B, FIG. 3C, FIG. 3D, and FIG. 3E are aberration diagrams showing a spherical aberration (SA), an astigmatism (AS), a distortion (DT), and a chromatic aberration of magnification (CC) respectively, of the example 2.

An endoscope objective optical system according to an example 2 will be described below. FIG. 3A is a cross-sectional view showing a lens arrangement of the endoscope objective optical system according to the present example.

In the present example, the endoscope objective optical system includes in order from an object side, a front group FL having a negative refractive power as a whole, an aperture stop S, and a rear group RL having a positive refractive power as a whole.

The endoscope objective optical system of the present example includes in order from the object side, a first lens L1 which is a planoconcave negative lens having a flat surface directed toward the object side, a second meniscus lens L2 having a positive refractive power and having a convex surface directed toward an image side, an infra-red absorption filter F1, the aperture stop S, a third lens L3 which is a biconvex positive lens, a fourth lens L4 which is a biconvex positive lens, a fifth meniscus lens L5 having a negative refractive power and having a concave surface directed toward the object side, a sixth lens L6 having a positive refractive power and having a convex surface directed toward the object side, and a CCD cover glass CG. In this example, I denotes an image pickup surface and IMG denotes an image pickup element.

The front group FL includes the first lens L1 having a negative refractive power and the second meniscus lens L2 having a positive refractive power. The rear group RL includes the third lens L3 having a positive refractive power, the fourth lens L4 having a positive refractive power, the fifth meniscus lens L5 having a negative refractive power, and the sixth lens L6 having a positive refractive power.

Moreover, a YAG laser cut coating is applied to an object side of the infra-red absorption filter F1, and an LD laser cut coating is applied to an image side of the infra-red absorption filter F1.

The fourth lens L4 having a positive refractive power and the fifth meniscus lens L5 having a negative refractive power are cemented and form a cemented lens CL1. The sixth lens L6 having a positive refractive power and the CCD cover glass CG are cemented.

FIG. 3B, FIG. 3C, FIG. 3D, and FIG. 3E are aberration diagrams showing a spherical aberration (SA), an astigmatism (AS), a distortion (DT), and a chromatic aberration of magnification (CC) respectively, of the example 2.

EXAMPLE 3

Figure 4A:
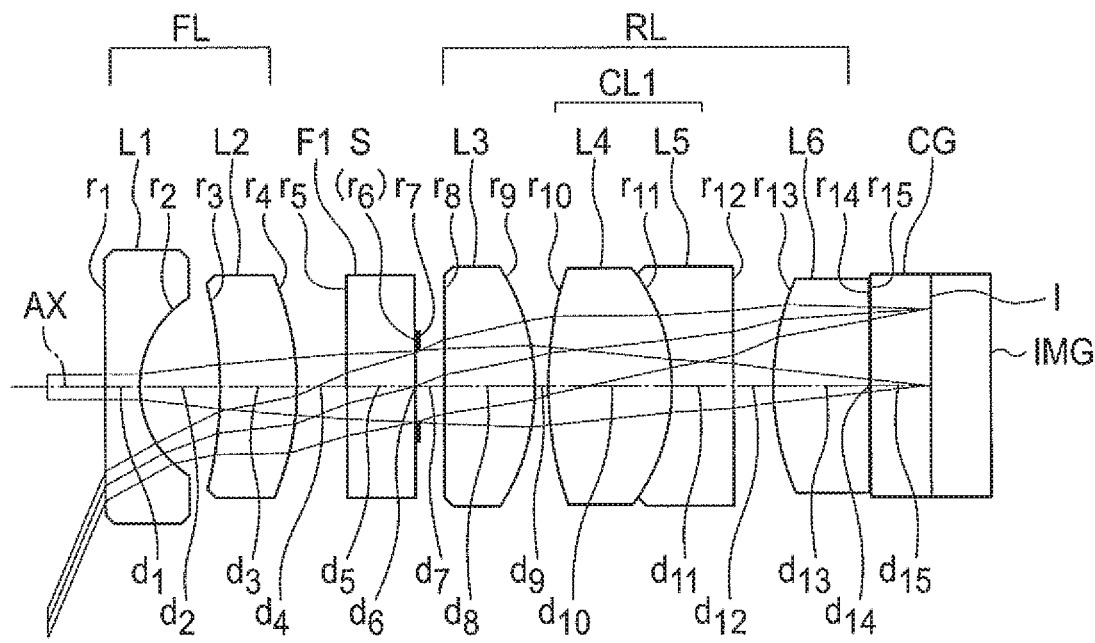
FIG. 4A is a cross-sectional view showing a lens arrangement of an endoscope objective optical system according to an example 3 of the present invention.
Figures 4B, 4C, 4D, 4E:
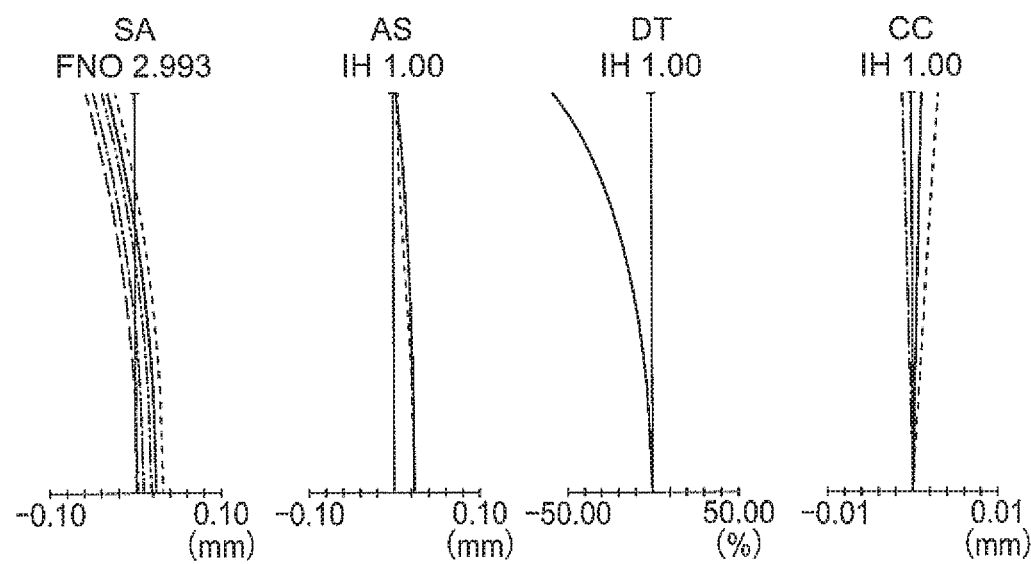
FIG. 4B, FIG. 4C, FIG. 4D, and FIG. 4E are aberration diagrams showing a spherical aberration (SA), an astigmatism (AS), a distortion (DT), and a chromatic aberration of magnification (CC) respectively, of the example 3.

An endoscope objective optical system according to an example 3 will be described below. FIG. 4A is a cross-sectional view showing a lens arrangement of the endoscope objective optical system according to the present example.

In the present example, the endoscope objective optical system includes in order from an object side, a front group FL having a negative refractive power as a whole, an aperture stop S, and a rear group RL having a positive refractive power as a whole.

The endoscope objective optical system of the present example includes in order from the object side, a first lens L1 which is a planoconcave negative lens having a flat surface directed toward the object side, a second meniscus lens L2 having a positive refractive power and having a convex surface directed toward an image side, an infra-red absorption filter F1, the aperture stop S, a third lens L3 which is a biconvex positive lens, a fourth lens L4 which is a biconvex positive lens, a fifth meniscus lens L5 having a negative refractive power and having a concave surface directed toward the object side, a sixth lens L6 having a positive refractive power and having a convex surface directed toward the object side, and a CCD cover glass CG. In this example, I denotes an image pickup surface and IMG denotes an image pickup element.

The front group FL includes the first lens L1 having a negative refractive power and the second meniscus lens L2 having a positive refractive power. The rear group RL includes the third lens L3 having a positive refractive power, the fourth lens L4 having a positive refractive power, the fifth meniscus lens L5 having a negative refractive power, and the sixth lens L6 having a positive refractive power.

Moreover, a YAG laser cut coating is applied to an object side of the infra-red absorption filter F1, and an LD laser cut coating is applied to an image side of the infra-red absorption filter F1.

The fourth lens L4 having a positive refractive power and the fifth meniscus lens L5 having a negative refractive power are cemented and form a cemented lens CL1. The sixth lens L6 having a positive refractive power and the CCD cover glass CG are cemented.

FIG. 4B, FIG. 4C, FIG. 4D, and FIG. 4E are aberration diagrams showing a spherical aberration (SA), an astigmatism (AS), a distortion (DT), and a chromatic aberration of magnification (CC) respectively, of the example 3.

EXAMPLE 4

Figure 5A:
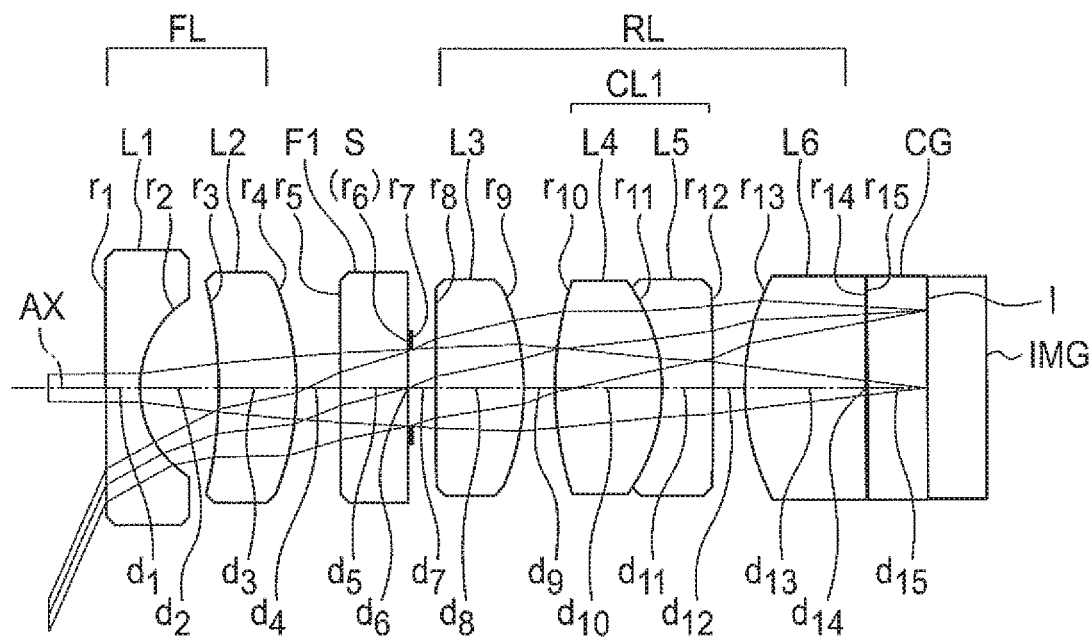
FIG. 5A is a cross-sectional view showing a lens arrangement of an endoscope objective optical system according to an example 4 of the present invention.
Figures 5B, 5C, 5D, 5E:
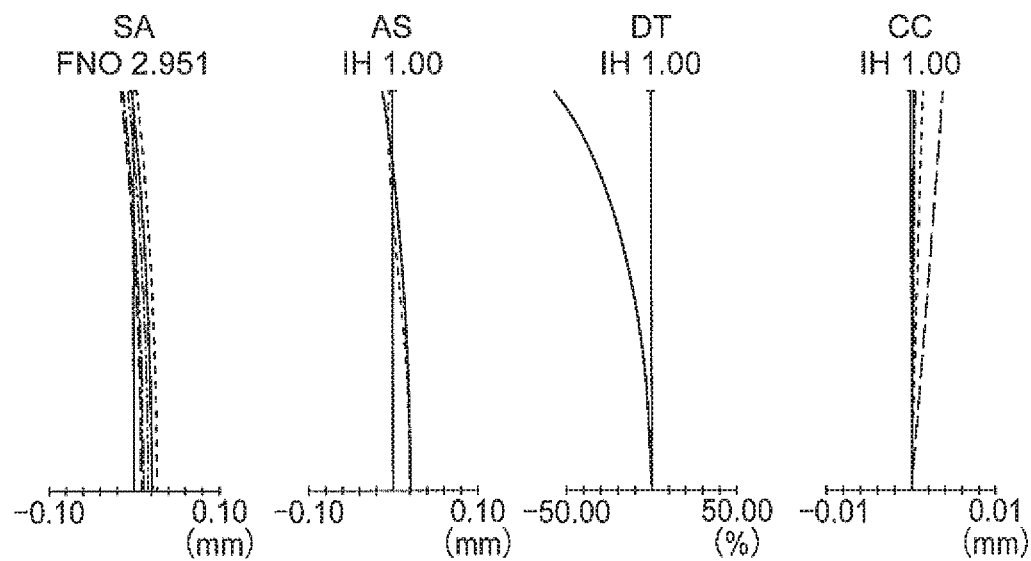
FIG. 5B, FIG. 5C, FIG. 5D, and FIG. 5E are aberration diagrams showing a spherical aberration (SA), an astigmatism (AS), a distortion (DT), and a chromatic aberration of magnification (CC) respectively, of the example 4.

An endoscope objective optical system according to an example 4 will be described below. FIG. 5A is a cross-sectional view showing a lens arrangement of the endoscope objective optical system according to the present example.

In the present example, the endoscope objective optical system includes in order from an object side, a front group FL having a negative refractive power as a whole, an aperture stop S, and a rear group RL having a positive refractive power as a whole.

The endoscope objective optical system of the present example includes in order from the object side, a first lens L1 which is a planoconcave negative lens having a flat surface directed toward the object side, a second meniscus lens L2 having a positive refractive power and having a convex surface directed toward an image side, an infra-red absorption filter F1, the aperture stop S, a third lens L3 which is a biconvex positive lens, a fourth lens L4 which is a biconvex positive lens, a fifth meniscus lens L5 having a negative refractive power and having a concave surface directed toward the object side, a sixth lens L6 having a positive refractive power and having a convex surface directed toward the object side, and a CCD cover glass CG. In this example, I denotes an image pickup surface and IMG denotes an image pickup element.

The front group FL includes the first lens L1 having a negative refractive power and the second meniscus lens L2 having a positive refractive power. The rear group RL includes the third lens L3 having a positive refractive power, the fourth lens L4 having a positive refractive power, the fifth meniscus lens L5 having a negative refractive power, and the sixth lens L6 having a positive refractive power.

Moreover, a YAG laser cut coating is applied to an object side of the infra-red absorption filter F1, and an LD laser cut coating is applied to an image side of the infra-red absorption filter F1.

The fourth lens L4 having a positive refractive power and the fifth meniscus lens L5 having a negative refractive power are cemented and form a cemented lens CL1. The sixth lens L6 having a positive refractive power and the CCD cover glass Cg are cemented.

FIG. 5B, FIG. 5C, FIG. 5D, and FIG. 5E are aberration diagrams showing a spherical aberration (SA), an astigmatism (AS), a distortion (DT), and a chromatic aberration of magnification (CC) respectively, of the example 4.

EXAMPLE 5

Figure 6A:
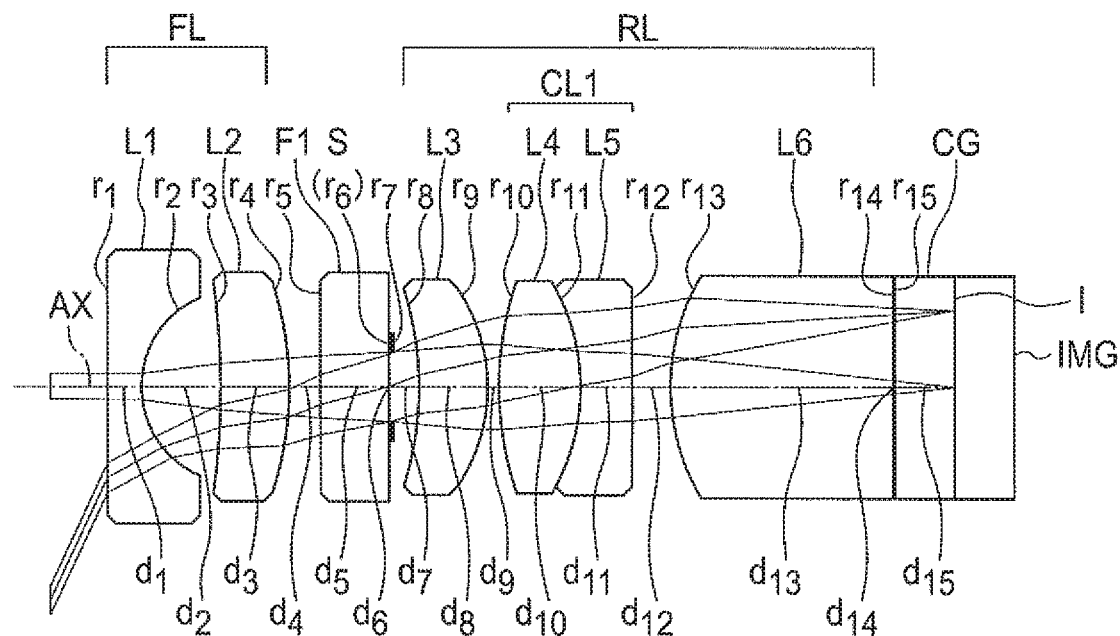
FIG. 6A is a cross-sectional view showing a lens arrangement of an endoscope objective optical system according to an example 5 of the present invention.
Figures 6B, 6C, 6D, 6E:
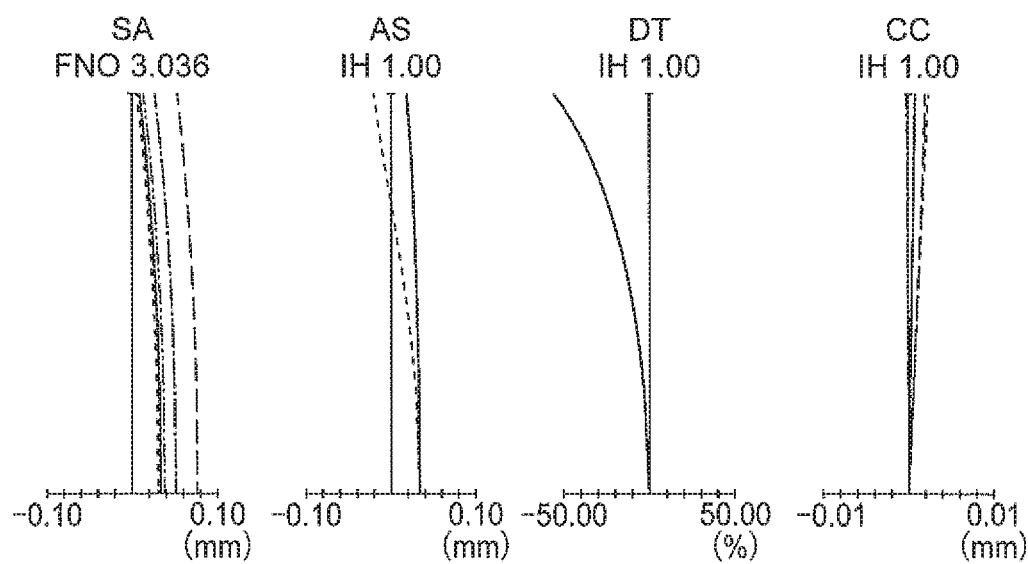
FIG. 6B, FIG. 6C, FIG. 6D, and FIG. 6E are aberration diagrams showing a spherical aberration (SA), an astigmatism (AS), a distortion (DT), and a chromatic aberration of magnification (CC) respectively, of the example 5.

An endoscope objective optical system according to an example 5 will be described below. FIG. 6A is a cross-sectional view showing a lens arrangement of the endoscope objective optical system according to the present example.

In the present example, the endoscope objective optical system includes in order from an object side, a front group FL having a negative refractive power as a whole, an aperture stop S, and a rear group RL having a positive refractive power as a whole.

The endoscope objective optical system of the present example includes in order from the object side, a first lens L1 which is a planoconcave negative lens having a flat surface directed toward the object side, a second meniscus lens L2 having a positive refractive power and having a convex surface directed toward an image side, an infra-red absorption filter F1, the aperture stop S, a third meniscus lens L3 having a positive refractive power and having a convex surface directed toward the image side, a fourth lens L4 which is a biconvex positive lens, a fifth meniscus lens L5 having a negative refractive power and having a concave surface directed toward the object side, a sixth lens L6 having a positive refractive power and having a convex surface directed toward the object side, and a CCD cover glass CG. In this example, I denotes an image pickup surface and IMG denotes an image pickup element.

The front group FL includes the first lens L1 having a negative refractive power and the second meniscus lens L2 having a positive refractive power. The rear group RL includes the third meniscus lens L3 having a positive refractive power, the fourth lens L4 having a positive refractive power, the fifth meniscus lens L5 having a negative refractive power, and the sixth lens L6 having a positive refractive power.

Moreover, a YAG laser cut coating is applied to an object side of the infra-red absorption filter F1, and an LD laser cut coating is applied to an image side of the infra-red absorption filter F1.

The fourth lens L4 having a positive refractive power and the fifth meniscus lens L5 having a negative refractive power are cemented and form a cemented lens CL1. The sixth lens L6 having a positive refractive power and the CCD cover glass CG are cemented.

FIG. 6B, FIG. 6C, FIG. 6D, and FIG. 6E are aberration diagrams showing a spherical aberration (SA), an astigmatism (AS), a distortion (DT), and a chromatic aberration of magnification (CC) respectively, of the example 5.

EXAMPLE 6

Figure 7A:
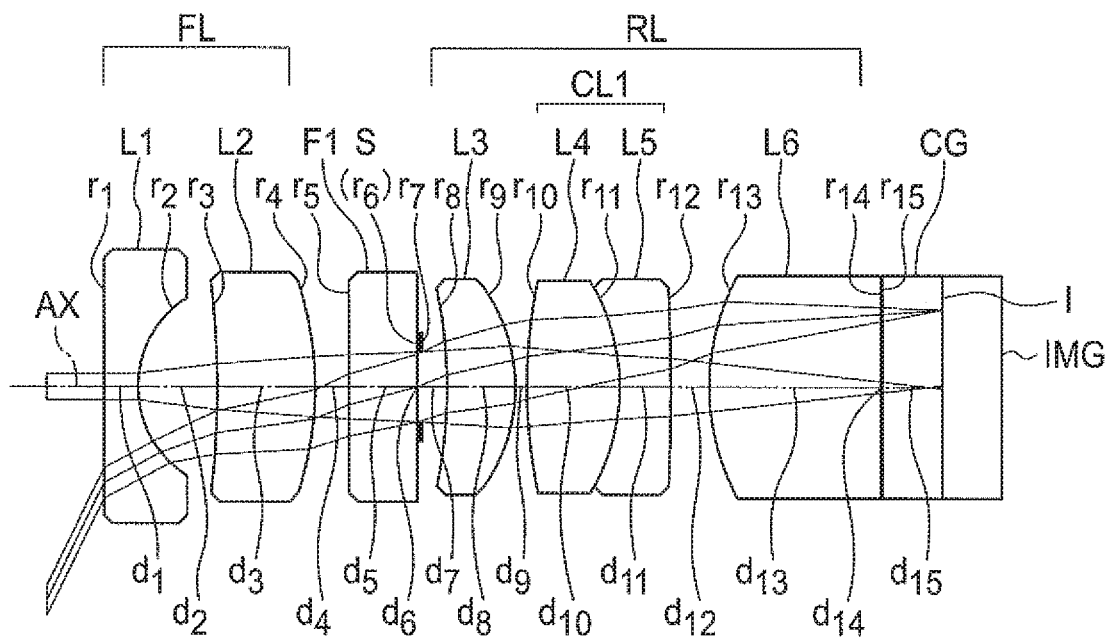
FIG. 7A is a cross-sectional view showing a lens arrangement of an endoscope objective optical system according to an example 6 of the present invention.
Figures 7B, 7C, 7D, 7E:
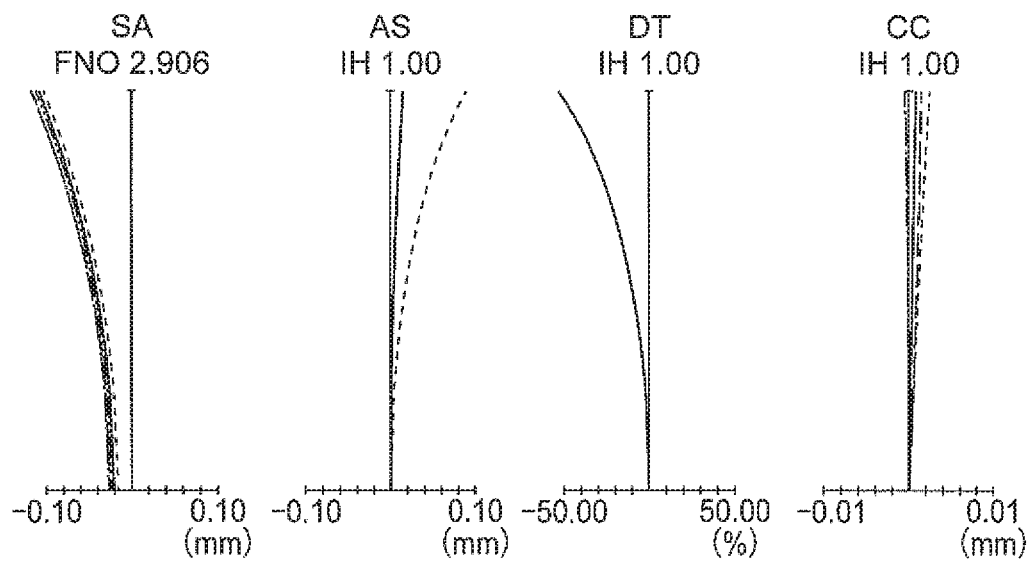
FIG. 7B, FIG. 7C, FIG. 7D, and FIG. 7E are aberration diagrams showing a spherical aberration (SA), an astigmatism (AS), a distortion (DT), and a chromatic aberration of magnification (CC) respectively, of the example 6.

An endoscope objective optical system according to an example 6 will be described below. FIG. 7A is a cross-sectional view showing a lens arrangement of the endoscope objective optical system according to the present example.

In the present example, the endoscope objective optical system includes in order from an object side, a front group FL having a negative refractive power as a whole, an aperture stop S, and a rear group RL having a positive refractive power as a whole.

The endoscope objective optical system of the present example includes in order from the object side, a first lens L1 which is a planoconcave negative lens having a flat surface directed toward the object side, a second meniscus lens L2 having a positive refractive power and having a convex surface directed toward an image side, an infra-red absorption filter F1, the aperture stop S, a third meniscus lens L3 having a positive refractive power and having a convex surface directed toward the image side, a fourth lens L4 which is a biconvex positive lens, a fifth meniscus lens L5 having a negative refractive power and having a concave surface directed toward the object side, a sixth lens L6 having a positive refractive power and having a convex surface directed toward the object side, and a CCD cover glass CG. In this example, I denotes an image pickup surface and IMG denotes an image pickup element.

The front group FL includes the first lens L1 having a negative refractive power and the second meniscus lens L2 having a positive refractive power. The rear group RL includes the third meniscus lens L3 having a positive refractive power, the fourth lens L4 having a positive refractive power, the fifth meniscus lens L5 having a negative refractive power, and the sixth lens L6 having a positive refractive power.

Moreover, a YAG laser cut coating is applied to an object side of the infra-red absorption filter F1, and an LD laser cut coating is applied to an image side of the infra-red absorption filter F1.

The fourth lens L4 having a positive refractive power and the fifth meniscus lens L5 having a negative refractive power are cemented and form a cemented lens CL1. The sixth lens L6 having a positive refractive power and the CCD cover glass CG are cemented.

FIG. 7B, FIG. 7C, FIG. 7D, and FIG. 7E are aberration diagrams showing a spherical aberration (SA), an astigmatism (AS), a distortion (DT), and a chromatic aberration of magnification (CC) respectively, of the example 6.

EXAMPLE 7

Figure 8A:
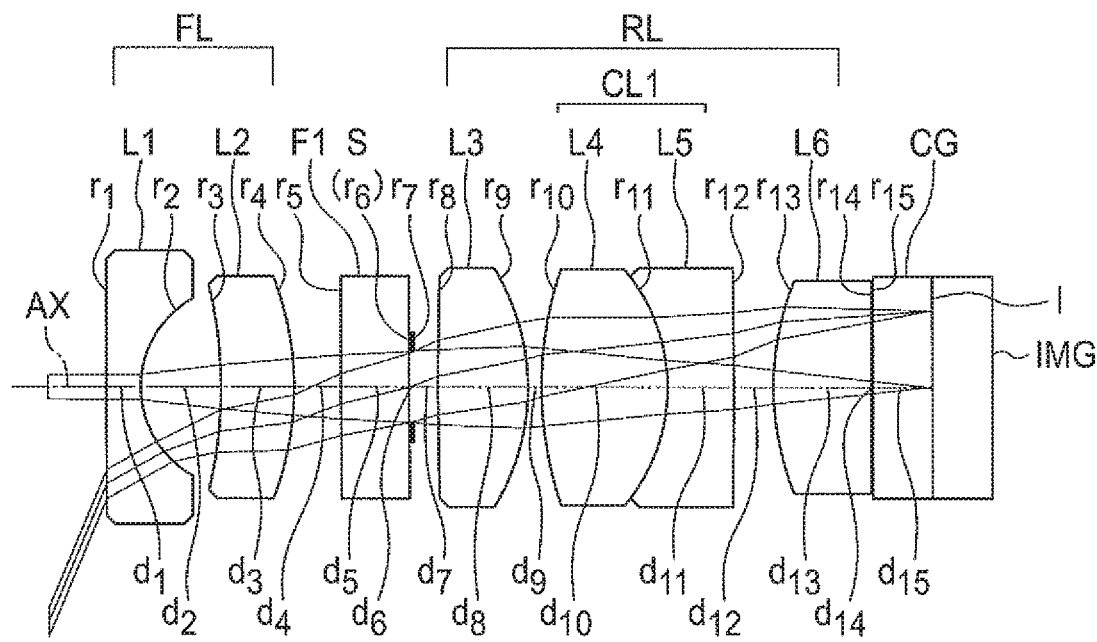
FIG. 8A is a cross-sectional view showing a lens arrangement of an endoscope objective optical system according to an example 7 of the present invention.
Figures 8B, 8C, 8D, 8E:
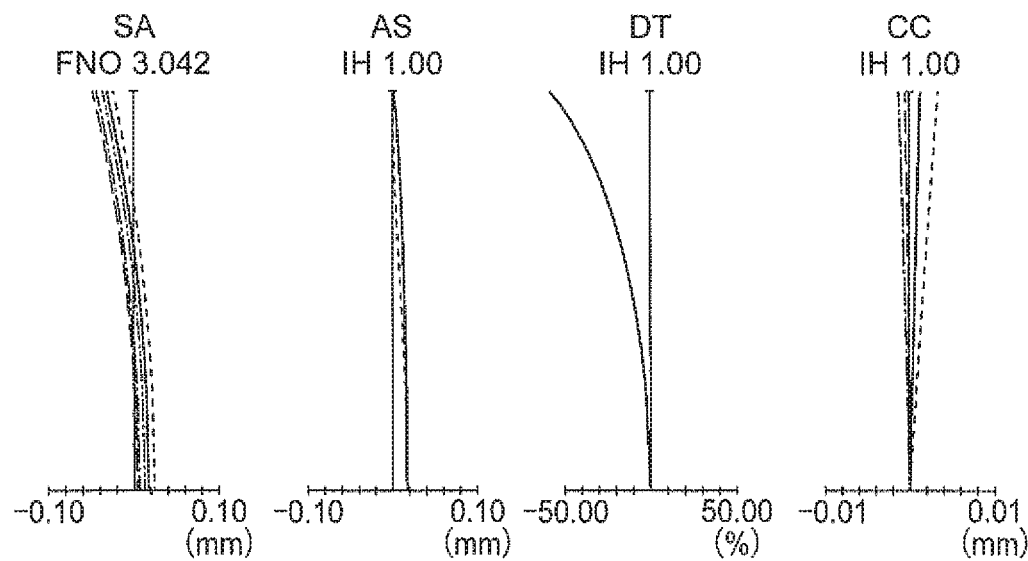
FIG. 8B, FIG. 8C, FIG. 8D, and FIG. 8E are aberration diagrams showing a spherical aberration (SA), an astigmatism (AS), a distortion (DT), and a chromatic aberration of magnification (CC) respectively, of the example 7.

An endoscope objective optical system according to an example 7 will be described below. FIG. 8A is a cross-sectional view showing a lens arrangement of the endoscope objective optical system according to the present example.

In the present example, the endoscope objective optical system includes in order from an object side, a front group FL having a negative refractive power as a whole, an aperture stop S, and a rear group RL having a positive refractive power as a whole.

The endoscope objective optical system of the present example includes in order from the object side, a first lens L1 which is a planoconcave negative lens having a flat surface directed toward the object side, a second meniscus lens L2 having a positive refractive power and having a convex surface directed toward an image side, an infra-red absorption filter F1, the aperture stop S, a third lens L3 which is a biconvex positive lens, a fourth lens L4 which is a biconvex positive lens, a fifth meniscus lens L5 having a negative refractive power and having a concave surface directed toward the object side, a sixth lens L6 having a positive refractive power and having a convex surface directed toward the object side, and a CCD cover glass CG. In this example, I denotes an image pickup surface and IMG denotes an image pickup element.

The front group FL includes the first lens L1 having a negative refractive power and the second meniscus lens L2 having a positive refractive power. The rear group RL includes the third lens L3 having a positive refractive power, the fourth lens L4 having a positive refractive power, the fifth meniscus lens L5 having a negative refractive power, and the sixth lens L6.

Moreover, a YAG laser cut coating is applied to an object side of the infra-red absorption filter F1, and an LD laser cut coating is applied to an image side of the infra-red absorption filter F1.

The fourth lens L4 having a positive refractive power and the fifth meniscus lens L5 having a negative refractive power are cemented and form a cemented lens CL1. The sixth lens L6 having a positive refractive power and the CCD cover glass CG are cemented.

FIG. 8B, FIG. 8C, FIG. 8D, and FIG. 8E are aberration diagrams showing a spherical aberration (SA), an astigmatism (AS), a distortion (DT), and a chromatic aberration of magnification (CC) respectively, of the example 7.

EXAMPLE 8

Figure 9A:
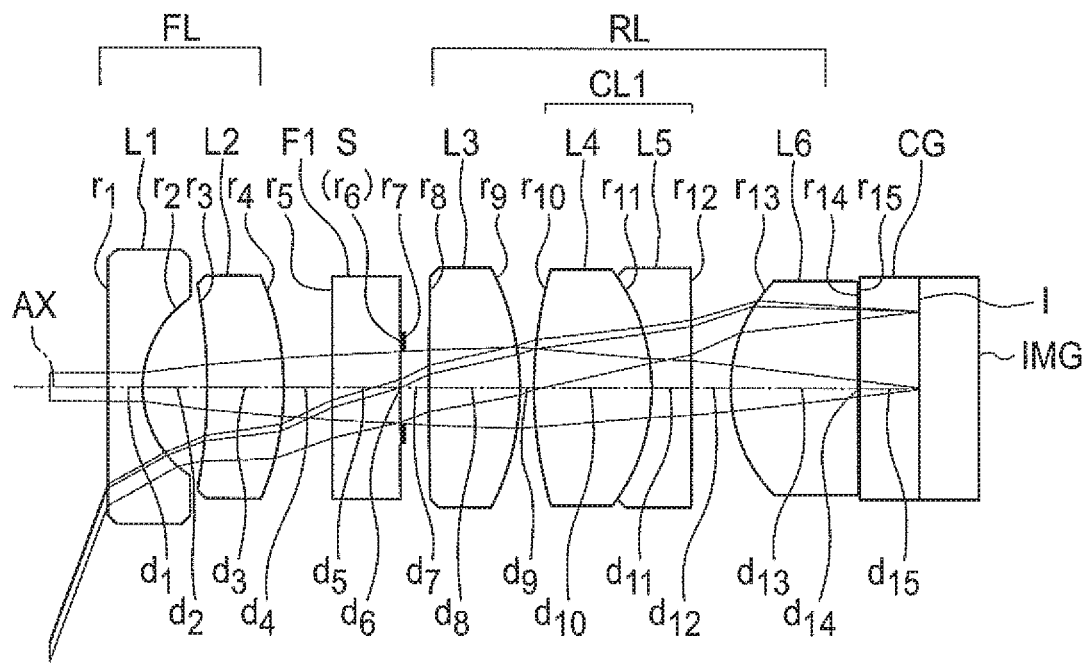
FIG. 9A is a cross-sectional view showing a lens arrangement of an endoscope objective optical system according to an example 8 of the present invention.
Figures 9B, 9C, 9D, 9E:
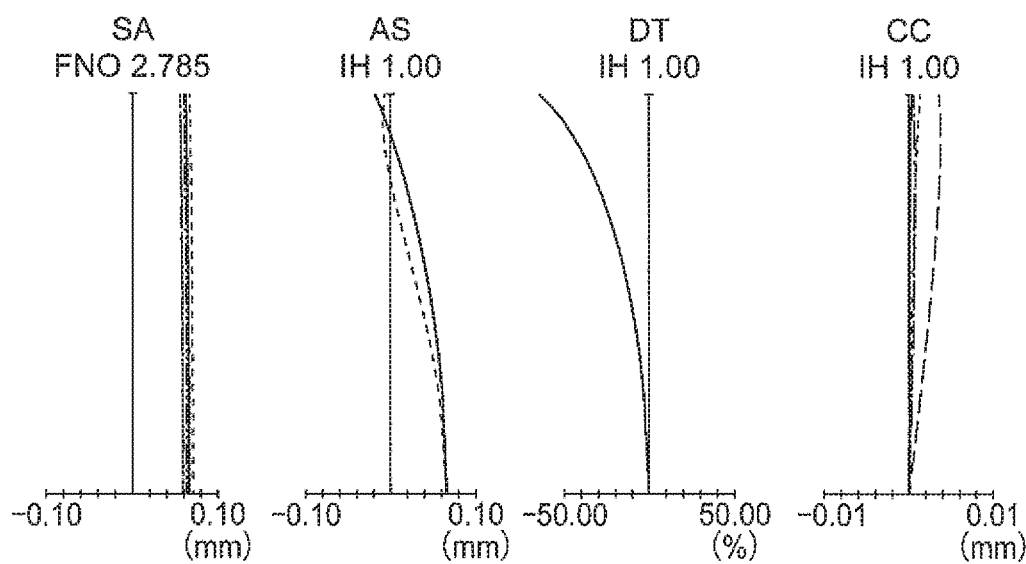
FIG. 9B, FIG. 9C, FIG. 9D, and FIG. 9E are aberration diagrams showing a spherical aberration (SA), an astigmatism (AS), a distortion (DT), and a chromatic aberration of magnification (CC) respectively, of the example 8.

An endoscope objective optical system according to an example 8 will be described below. FIG. 9A is a cross-sectional view showing a lens arrangement of the endoscope objective optical system according to the present example.

In the present example, the endoscope objective optical system includes in order from an object side, a front group FL having a negative refractive power as a whole, an aperture stop S, and a rear group RL having a positive refractive power as a whole.

The endoscope objective optical system of the present example includes in order from the object side, a first lens L1 which is a planoconcave negative lens having a flat surface directed toward the object side, a second meniscus lens L2 having a positive refractive power and having a convex surface directed toward an image side, an infra-red absorption filter F1, the aperture stop S, a third lens L3 which is a biconvex positive lens, a fourth lens L4 which is a biconvex positive lens, a fifth meniscus lens L5 having a negative refractive power and having a concave surface directed toward the object side, a sixth lens L6 having a positive refractive power and having a convex surface directed toward the object side, and a CCD cover glass CG. In this example, I denotes an image pickup surface and IMG denotes an image pickup element.

The front group FL includes the first lens L1 having a negative refractive power and the second meniscus lens L2 having a positive refractive power. The rear group RL includes the third lens L3 having a positive refractive power, the fourth lens L4 having a positive refractive power, the fifth meniscus lens L5 having a negative refractive power, and the sixth lens L6 having a positive refractive power.

Moreover, a YAG laser cut coating is applied to an object side of the infra-red absorption filter F1, and an LD laser cut coating is applied to an image side of the infra-red absorption filter F1.

The fourth lens L4 having a positive refractive power and the fifth meniscus lens L5 having a negative refractive power are cemented and form a cemented lens CL1. The sixth lens L6 having a positive refractive power and the CCD cover glass CG are cemented.

FIG. 9B, FIG. 9C, FIG. 9D, and FIG. 9E are aberration diagrams showing a spherical aberration (SA), an astigmatism (AS), a distortion (DT), and a chromatic aberration of magnification (CC) respectively, of the example 8.

EXAMPLE 9

Figure 10A:
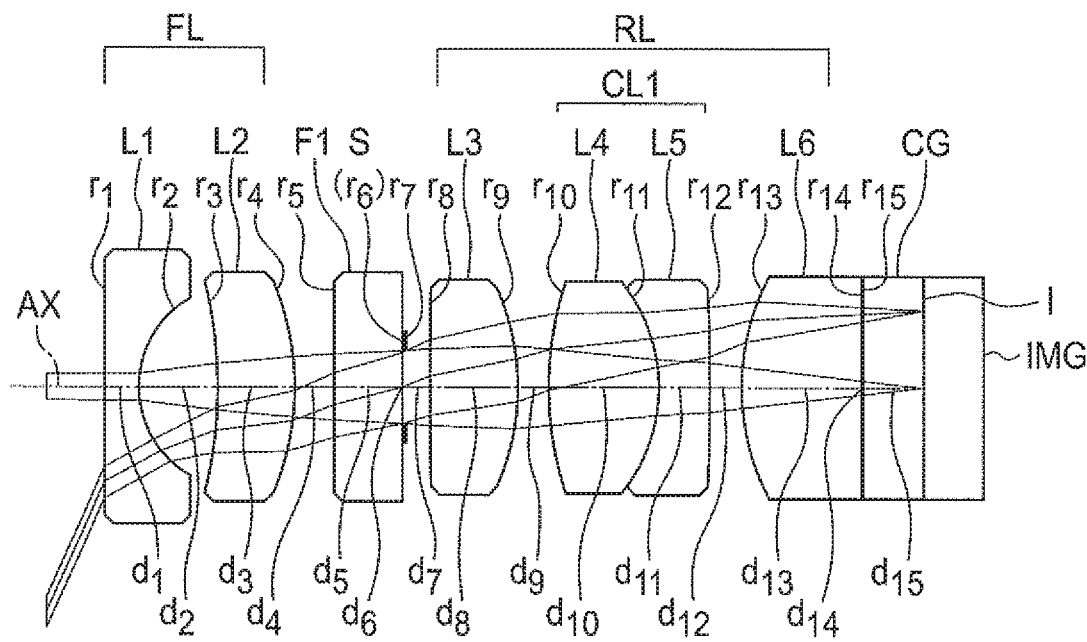
FIG. 10A is a cross-sectional view showing a lens arrangement of an endoscope objective optical system according to an example 9 of the present invention.
Figures 10B, 10C, 10D, 10E:
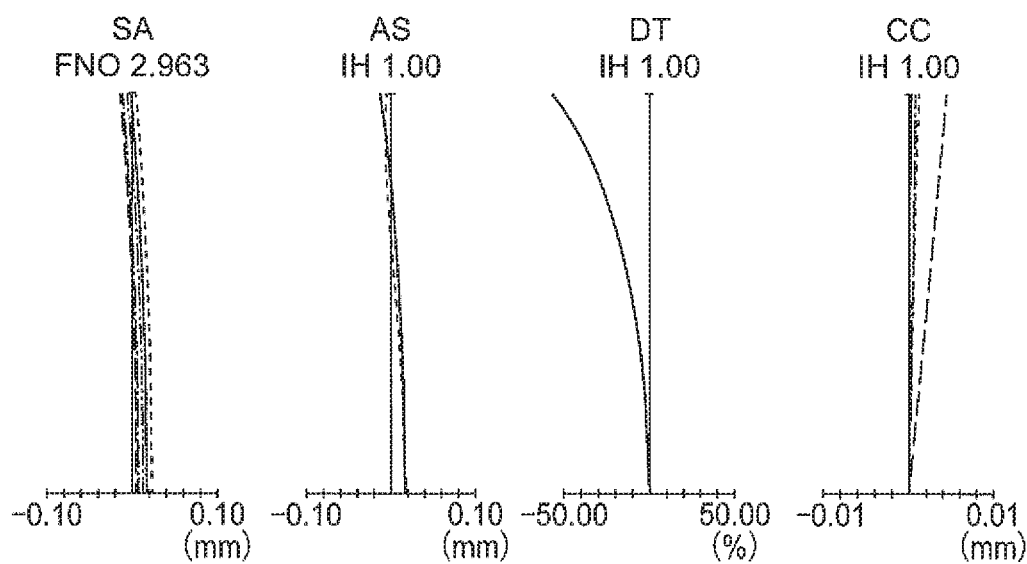
FIG. 10B, FIG. 10C, FIG. 10D, and FIG. 10E are aberration diagrams showing a spherical aberration (SA), an astigmatism (AS), a distortion (DT), and a chromatic aberration of magnification (CC) respectively, of the example 9.

An endoscope objective optical system according to an example 9 will be described below. FIG. 10A is a cross-sectional view showing a lens arrangement of the endoscope objective optical system according to the present example.

In the present example, the endoscope objective optical system includes in order from an object side, a front group FL having a negative refractive power as a whole, an aperture stop S, and a rear group RL having a positive refractive power as a whole.

The endoscope objective optical system of the present example includes in order from the object side, a first lens L1 which is a planoconcave negative lens having a flat surface directed toward the object side, a second meniscus lens L2 having a positive refractive power and having a convex surface directed toward an image side, an infra-red absorption filter F1, the aperture stop S, a third lens L3 which is a biconvex positive lens, a fourth lens L4 which is a biconvex positive lens, a fifth meniscus lens L5 having a negative refractive power and having a concave surface directed toward the object side, a sixth lens L6 having a positive refractive power and having a convex surface directed toward the object side, and a CCD cover glass CG. In this example, I denotes an image pickup surface and IMG denotes an image pickup element.

The front group FL includes the first lens L1 having a negative refractive power and the second meniscus lens L2 having a positive refractive power. The rear group RL includes the third lens L3 having a positive refractive power, the fourth lens L4 having a positive refractive power, the fifth meniscus lens L5 having a negative refractive power, and the sixth lens L6 having a positive refractive power.

Moreover, a YAG laser cut coating is applied to an object side of the infra-red absorption filter F1, and an LD laser cut coating is applied to an image side of the infra-red absorption filter F1.

The fourth lens L4 having a positive refractive power and the fifth meniscus lens L5 having a negative refractive power are cemented and form a cemented lens CL1. The sixth lens L6 having a positive refractive power and the CCD cover glass CG are cemented.

FIG. 10B, FIG. 10C, FIG. 10D, and FIG. 10E are aberration diagrams showing a spherical aberration (SA), an astigmatism (AS), a distortion (DT), and a chromatic aberration of magnification (CC) respectively, of the example 9.

EXAMPLE 10

Figure 11A:
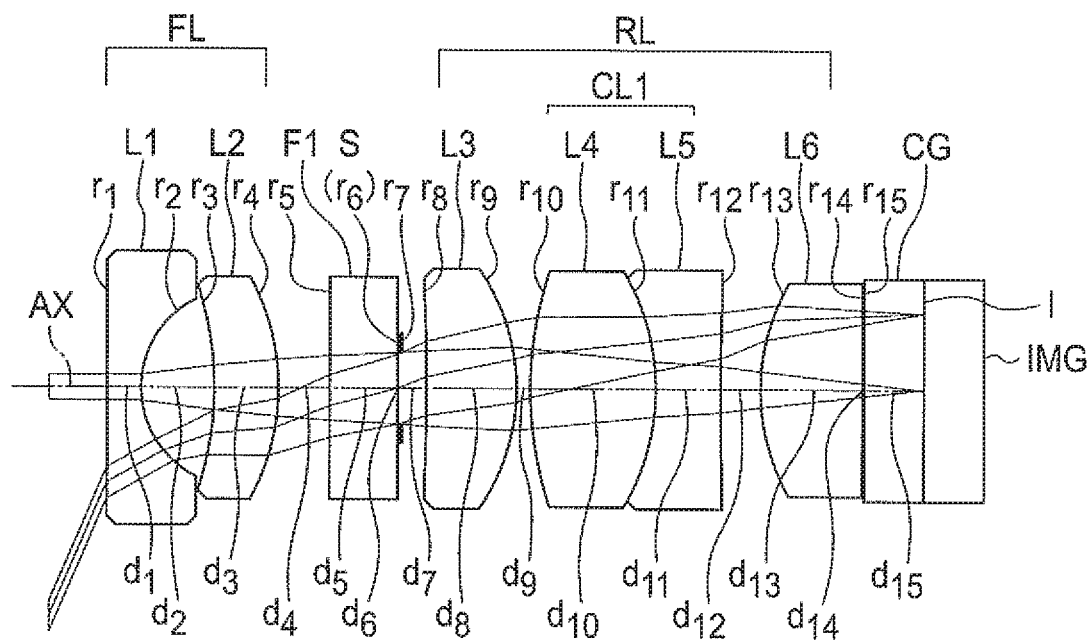
FIG. 11A is a cross-sectional view showing a lens arrangement of an endoscope objective optical system according to an example 10 of the present invention.
Figures 11B, 11C, 11D, 11E:
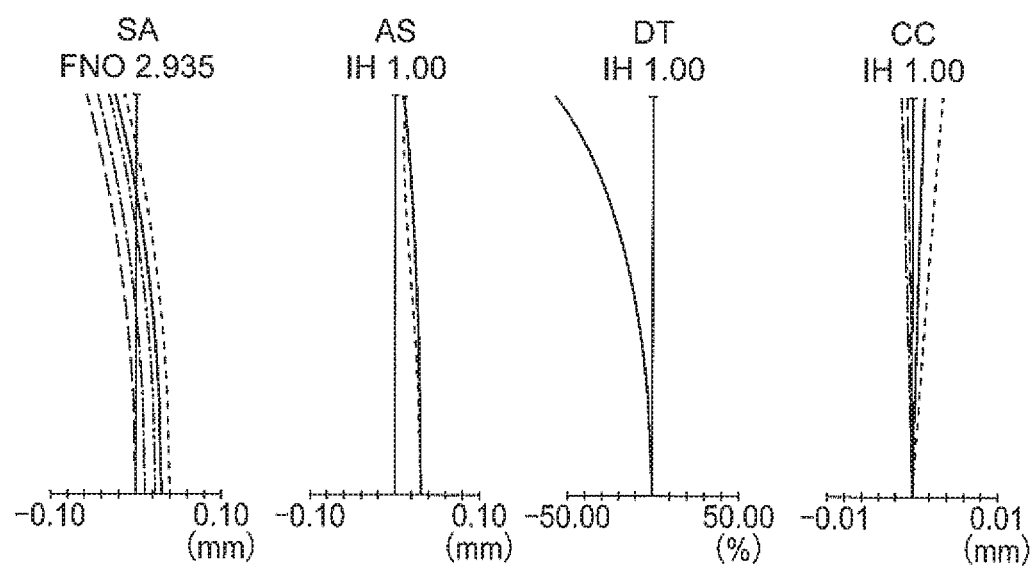
FIG. 11B, FIG. 11C, FIG. 11D, and FIG. 11E are aberration diagrams showing a spherical aberration (SA), an astigmatism (AS), a distortion (DT), and a chromatic aberration of magnification (CC) respectively, of the example 10.

An endoscope objective optical system according to an example 10 will be described below. FIG. 11A is a cross-sectional view showing a lens arrangement of the endoscope objective optical system according to the present example.

In the present example, the endoscope objective optical system includes in order from an object side, a front group FL having a negative refractive power as a whole, an aperture stop S, and a rear group RL having a positive refractive power as a whole.

The endoscope objective optical system of the present example includes in order from the object side, a first lens L1 which is a planoconcave negative lens having a flat surface directed toward the object side, a second meniscus lens L2 having a positive refractive power and having a convex surface directed toward an image side, an infra-red absorption filter F1, the aperture stop S, a third meniscus lens L3 having a positive refractive power and having a convex surface directed toward an image side, a fourth lens L4 which is a biconvex positive lens, a fifth lens L5 which is a biconcave negative lens, a sixth lens L6 having a positive refractive power and having a convex surface directed toward the object side, and a CCD cover glass CG. In this example, I denotes an image pickup surface and IMG denotes an image pickup element.

The front group FL includes the first lens L1 having a negative refractive power and the second meniscus lens L2 having a positive refractive power. The rear group RL includes the third meniscus lens L3 having a positive refractive power, the fourth lens L4 having a positive refractive power, the fifth lens L5 having a negative refractive power, and the sixth lens L6 having a positive refractive power.

Moreover, a YAG laser cut coating is applied to an object side of the infra-red absorption filter F1, and an LD laser cut coating is applied to an image side of the infra-red absorption filter F1.

The fourth lens L4 having a positive refractive power and the fifth lens L5 having a negative refractive power are cemented and forma cemented lens CL1. The sixth lens L6 having a positive refractive power and the CCD cover glass CG are cemented.

FIG. 11B, FIG. 11C, FIG. 11D, and FIG. 11E are aberration diagrams showing a spherical aberration (SA), an astigmatism (AS), a distortion (DT), and a chromatic aberration of magnification (CC) respectively, of the example 10.

EXAMPLE 11

Figure 12A:
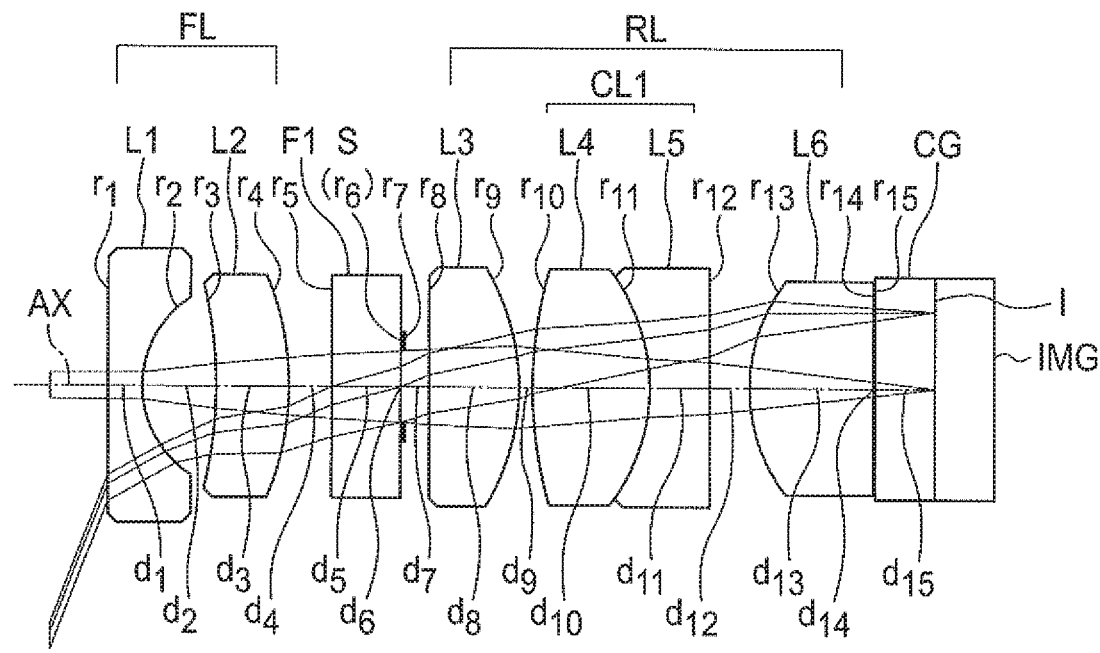
FIG. 12A is a cross-sectional view showing a lens arrangement of an endoscope objective optical system according to an example 11 of the present invention.
Figures 12B, 12C, 12D, 12E:
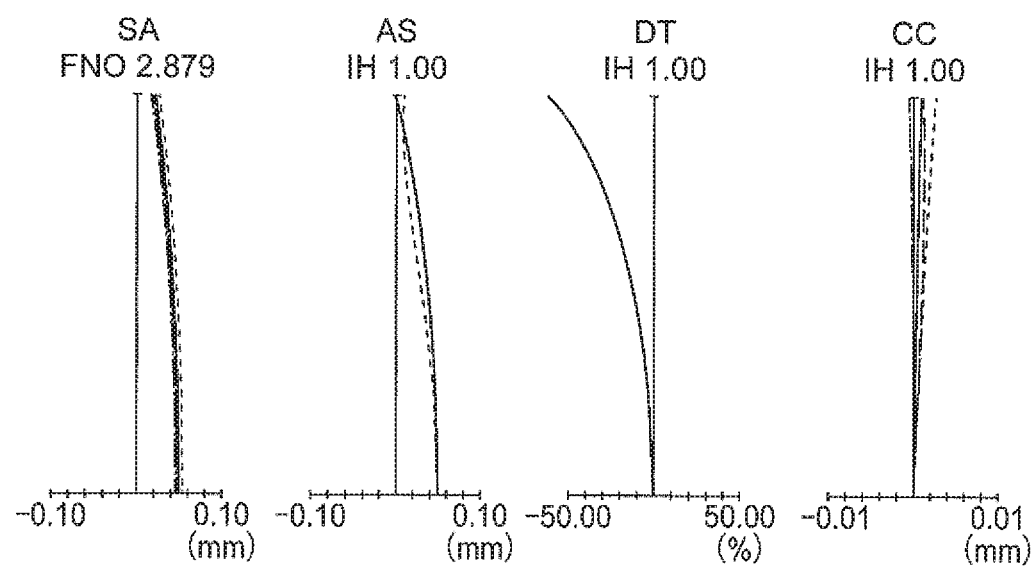
FIG. 12B, FIG. 12C, FIG. 12D, and FIG. 12E are aberration diagrams showing a spherical aberration (SA), an astigmatism (AS), a distortion (DT), and a chromatic aberration of magnification (CC) respectively, of the example 11.

An endoscope objective optical system according to an example 11 will be described below. FIG. 12A is a cross-sectional view showing a lens arrangement of the endoscope objective optical system according to the present example.

In the present example, the endoscope objective optical system includes in order from an object side, a front group FL having a negative refractive power as a whole, an aperture stop S, and a rear group RL having a positive refractive power as a whole.

The endoscope objective optical system of the present example includes in order from the object side, a first lens L1 which is a planoconcave negative lens having a flat surface directed toward the object side, a second meniscus lens L2 having a positive refractive power and having a convex surface directed toward an image side, an infra-red absorption filter F1, the aperture stop S, a third meniscus lens L3 having a positive refractive power and having a convex surface directed toward the image side, a fourth lens L4 which is a biconvex positive lens, a fifth lens L5 which is a biconcave negative lens, a sixth lens L6 having a positive refractive power and having a convex surface directed toward the object side, and a CCD cover glass CG. In this example, I denotes an image pickup surface and IMG denotes an image pickup element.

The front group FL includes the first lens L1 having a negative refractive power and the second meniscus lens L2 having a positive refractive power. The rear group RL includes the third meniscus lens L3 having a positive refractive power, the fourth lens L4 having a positive refractive power, the fifth lens L5 having a negative refractive power, and the sixth lens L6 having a positive refractive power.

Moreover, a YAG laser cut coating is applied to an object side of the infra-red absorption filter F1, and an LD laser cut coating is applied to an image side of the infra-red absorption filter F1.

The fourth lens L4 having a positive refractive power and the fifth lens L5 having a negative refractive power are cemented and forma cemented lens CL1. The sixth lens L6 having a positive refractive power and the CCD cover glass CG are cemented.

FIG. 12B, FIG. 12C, FIG. 12D, and FIG. 12E are aberration diagrams showing a spherical aberration (SA), an astigmatism (AS), a distortion (DT), and a chromatic aberration of magnification (CC) respectively, of the example 11.

EXAMPLE 12

Figure 13A:
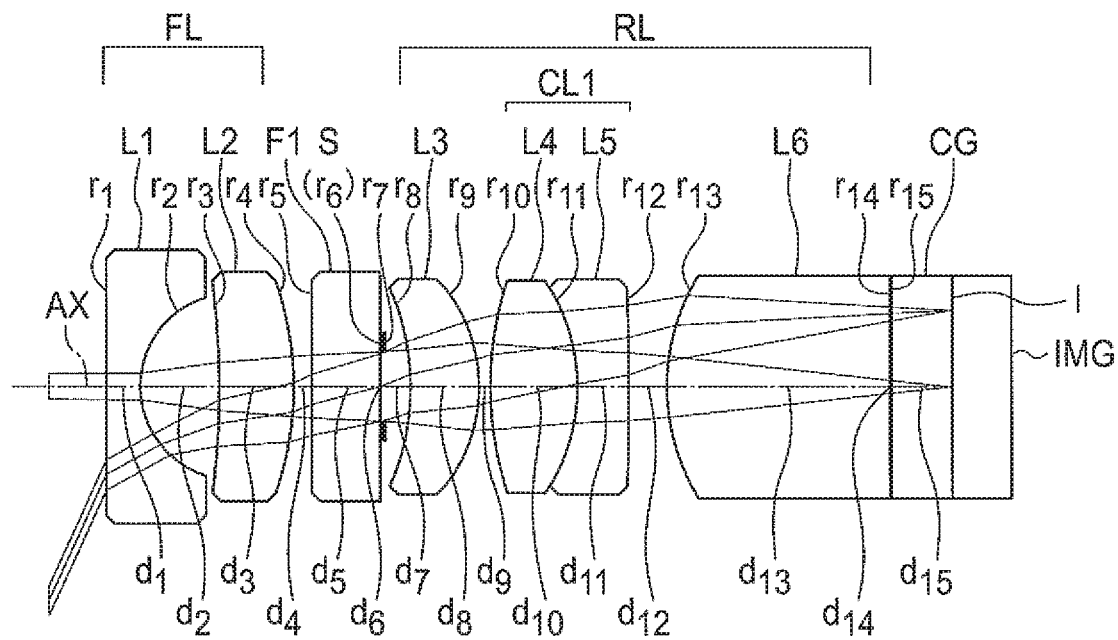
FIG. 13A is a cross-sectional view showing a lens arrangement of an endoscope objective optical system according to an example 12 of the present invention.
Figures 13B, 13C, 13D, 13E:
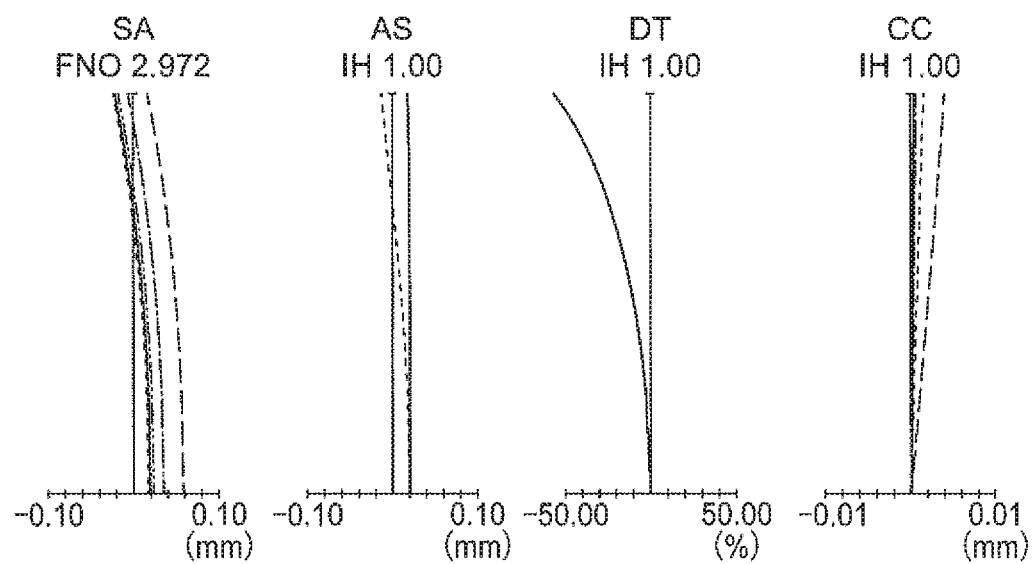
FIG. 13B, FIG. 13C, FIG. 13D, and FIG. 13E are aberration diagrams showing a spherical aberration (SA), an astigmatism (AS), a distortion (DT), and a chromatic aberration of magnification (CC) respectively, of the example 12.

An endoscope objective optical system according to an example 12 will be described below. FIG. 13A is a cross-sectional view showing a lens arrangement of the endoscope objective optical system according to the present example.

The endoscope objective optical system of the present example includes in order from an object side, a first lens L1 which is a planoconcave negative lens having a flat surface directed toward the object side, a second meniscus lens L2 having a positive refractive power and having a convex surface directed toward an image side, an infra-red absorption filter F1, an aperture stop S, a third meniscus lens L3 having a positive refractive power and having a convex surface directed toward an image side, a fourth lens L4 which is a biconvex positive lens, a fifth meniscus lens L5 having a negative refractive power and having a concave surface directed toward the object side, a sixth lens L6 having a positive refractive power and having a convex surface directed toward the object side, and a CCD cover glass CG. In this example, I denotes an image pickup surface and IMG denotes an image pickup element.

The front group FL includes the first lens L1 having a negative refractive power and the second meniscus lens L2 having a positive refractive power. The rear group RL includes the third meniscus lens L3 having a positive refractive power, the fourth lens L4 having a positive refractive power, the fifth meniscus lens L5 having a negative refractive power, and the sixth lens L6 having a positive refractive power.

Moreover, a YAG laser cut coating is applied to an object side of the infra-red absorption filter F1, and an LD laser cut coating is applied to an image side of the infra-red absorption filter F1.

The fourth lens L4 having a positive refractive power and the fifth meniscus lens L5 having a negative refractive power are cemented and form a cemented lens CL1. The sixth lens L6 having a positive refractive power and the CCD cover glass CG are cemented.

FIG. 13B, FIG. 13C, FIG. 13D, and FIG. 13E are aberration diagrams showing a spherical aberration (SA), an astigmatism (AS), a distortion (DT), and a chromatic aberration of magnification (CC) respectively, of the example 12.

Numerical data of each example described above is shown below. In symbols, r denotes radius of curvature of each lens surface, d denotes a distance between respective lens surfaces, nd denotes a refractive index of each lens for a d-line, vd denotes an Abbe number for each lens, FNo denotes an F number, ω denotes a half angle of view, and IH denotes an image height.

EXAMPLE 1

Unit mm

Surface data

| Surface no. | r | d | nd | vd |
|---|---|---|---|---|
| 1 | ∞ | 0.45 | 1.888 | 40.76 |
| 2 | 1.361 | 1.07 | | |
| 3 | −5.665 | 0.98 | 1.972 | 17.47 |
| 4 | −3.734 | 0.58 | | |
| 5 | ∞ | 0.89 | 1.496 | 75.00 |
| 6 (Stop) | ∞ | 0.07 | | |
| 7 | ∞ | 0.31 | | |
| 8 | 546.967 | 1.18 | 1.888 | 40.76 |
| 9 | −2.932 | 0.17 | | |
| 10 | 5.234 | 1.52 | 1.700 | 55.53 |
| 11 | −2.540 | 0.67 | 1.972 | 17.47 |
| 12 | −393.697 | 0.51 | | |
| 13 | 3.064 | 1.57 | 1.518 | 64.14 |
| 14 | ∞ | 0.02 | 1.515 | 64.00 |
| 15 | ∞ | 0.78 | 1.507 | 63.26 |
| 16 (Image pickup surface) | ∞ | 0.00 | | |

Various data

| | |
|---|---|
| FNo. | 2.994 |
| ω (half angle of view) | 66.6° |
| IH (mm) | 1 |

EXAMPLE 2

Unit mm

Surface data

| Surface no. | r | d | nd | vd |
|---|---|---|---|---|
| 1 | ∞ | 0.45 | 1.888 | 40.76 |
| 2 | 1.407 | 1.03 | | |
| 3 | −5.953 | 0.99 | 1.972 | 17.47 |
| 4 | −4.100 | 0.68 | | |
| 5 | ∞ | 0.89 | 1.496 | 75.00 |
| 6 (Stop) | ∞ | 0.07 | | |
| 7 | ∞ | 0.30 | | |
| 8 | 27.943 | 1.15 | 1.888 | 40.76 |
| 9 | −3.091 | 0.41 | | |
| 10 | 4.988 | 1.40 | 1.700 | 55.53 |
| 11 | −2.461 | 0.67 | 1.972 | 17.47 |
| 12 | −718.021 | 0.42 | | |
| 13 | 3.100 | 1.56 | 1.518 | 64.14 |
| 14 | ∞ | 0.02 | 1.515 | 64.00 |
| 15 | ∞ | 0.78 | 1.507 | 63.26 |
| 16 (Image pickup surface) | ∞ | 0.00 | | |

Various data

| | |
|---|---|
| FNo. | 3.023 |
| ω (half angle of view) | 65.6° |
| IH (mm) | 1 |

EXAMPLE 3

Unit mm

Surface data

| Surface no. | r | d | nd | vd |
|---|---|---|---|---|
| 1 | ∞ | 0.45 | 1.888 | 40.76 |
| 2 | 1.366 | 1.05 | | |
| 3 | −5.321 | 1.00 | 1.972 | 17.47 |
| 4 | −3.677 | 0.65 | | |
| 5 | ∞ | 0.89 | 1.496 | 75.00 |
| 6 (Stop) | ∞ | 0.07 | | |
| 7 | ∞ | 0.31 | | |
| 8 | 283.432 | 1.18 | 1.888 | 40.76 |
| 9 | −2.872 | 0.18 | | |
| 10 | 4.817 | 1.62 | 1.700 | 55.53 |
| 11 | −2.541 | 0.80 | 1.972 | 17.47 |
| 12 | −589.562 | 0.51 | | |
| 13 | 3.511 | 1.24 | 1.518 | 64.14 |
| 14 | ∞ | 0.02 | 1.515 | 64.00 |
| 15 | ∞ | 0.78 | 1.507 | 63.26 |
| 16 (Image pickup surface) | ∞ | 0.00 | | |

Various data

| | |
|---|---|
| FNo. | 2.993 |
| ω (half angle of view) | 67.0° |
| IH (mm) | 1 |

EXAMPLE 4

Unit mm

Surface data

| Surface no. | r | d | nd | νd |
|---|---|---|---|---|
| 1 | ∞ | 0.45 | 1.888 | 40.76 |
| 2 | 1.368 | 1.03 | | |
| 3 | −5.818 | 1.00 | 1.972 | 17.47 |
| 4 | −3.680 | 0.57 | | |
| 5 | ∞ | 0.89 | 1.496 | 75.00 |
| 6 (Stop) | ∞ | 0.07 | | |
| 7 | ∞ | 0.30 | | |
| 8 | 119.771 | 1.15 | 1.888 | 40.76 |
| 9 | −3.155 | 0.41 | | |
| 10 | 4.431 | 1.39 | 1.700 | 55.53 |
| 11 | −2.320 | 0.67 | 1.972 | 17.47 |
| 12 | −51.038 | 0.42 | | |
| 13 | 3.100 | 1.56 | 1.518 | 64.14 |
| 14 | ∞ | 0.02 | 1.515 | 64.00 |
| 15 | ∞ | 0.78 | 1.507 | 63.26 |
| 16 (Image pickup surface) | ∞ | 0.00 | | |

Various data

| | |
|---|---|
| FNo. | 2.951 |
| ω (half angle of view) | 65.7° |
| IH (mm) | 1 |

EXAMPLE 5

Unit mm

Surface data

| Surface no. | r | d | nd | νd |
|---|---|---|---|---|
| 1 | ∞ | 0.45 | 1.888 | 40.76 |
| 2 | 1.262 | 1.03 | | |
| 3 | −10.178 | 0.89 | 1.972 | 17.47 |
| 4 | −4.500 | 0.41 | | |
| 5 | ∞ | 0.89 | 1.496 | 75.00 |
| 6 (Stop) | ∞ | 0.07 | | |
| 7 | ∞ | 0.32 | | |
| 8 | −4.233 | 0.90 | 1.888 | 40.76 |
| 9 | −2.290 | 0.15 | | |
| 10 | 4.248 | 1.07 | 1.700 | 55.53 |
| 11 | −2.700 | 0.67 | 1.972 | 17.47 |
| 12 | −195.236 | 0.50 | | |
| 13 | 2.838 | 2.89 | 1.518 | 64.14 |
| 14 | ∞ | 0.02 | 1.515 | 64.00 |
| 15 | ∞ | 0.78 | 1.507 | 63.26 |
| 16 (Image pickup surface) | ∞ | 0.00 | | |

Various data

| | |
|---|---|
| FNo. | 3.036 |
| Ω (half angle of view) | 64.8° |
| IH (mm) | 1 |

EXAMPLE 6

Unit mm

Surface data

| Surface no. | r | d | nd | νd |
|---|---|---|---|---|
| 1 | ∞ | 0.45 | 1.888 | 40.76 |
| 2 | 1.366 | 1.03 | | |
| 3 | −12.038 | 1.27 | 1.972 | 17.47 |
| 4 | −4.400 | 0.44 | | |
| 5 | ∞ | 0.89 | 1.496 | 75.00 |
| 6 (Stop) | ∞ | 0.07 | | |
| 7 | ∞ | 0.32 | | |
| 8 | −6.155 | 0.90 | 1.888 | 40.76 |
| 9 | −2.227 | 0.15 | | |
| 10 | 6.630 | 1.20 | 1.700 | 55.53 |
| 11 | −2.660 | 0.67 | 1.972 | 17.47 |
| 12 | −28.953 | 0.50 | | |
| 13 | 3.030 | 2.22 | 1.518 | 64.14 |
| 14 | ∞ | 0.02 | 1.515 | 64.00 |
| 15 | ∞ | 0.78 | 1.507 | 63.26 |
| 16 (Image pickup surface) | ∞ | 0.00 | | |

Various data

| | |
|---|---|
| FNo. | 2.906 |
| ω (half angle of view) | 63.9° |
| IH (mm) | 1 |

EXAMPLE 7

Unit mm

Surface data

| Surface no. | r | d | nd | νd |
|---|---|---|---|---|
| 1 | ∞ | 0.45 | 1.888 | 40.76 |
| 2 | 1.329 | 1.05 | | |
| 3 | −5.692 | 0.95 | 1.972 | 17.47 |
| 4 | −3.999 | 0.60 | | |
| 5 | ∞ | 0.89 | 1.496 | 75.00 |
| 6 (Stop) | ∞ | 0.07 | | |
| 7 | ∞ | 0.31 | | |
| 8 | 46.525 | 1.18 | 1.888 | 40.76 |
| 9 | −2.953 | 0.18 | | |
| 10 | 4.709 | 1.64 | 1.700 | 55.53 |
| 11 | −2.400 | 0.85 | 1.972 | 17.47 |
| 12 | −87.314 | 0.51 | | |
| 13 | 3.700 | 1.27 | 1.518 | 64.14 |
| 14 | ∞ | 0.02 | 1.515 | 64.00 |
| 15 | ∞ | 0.78 | 1.507 | 63.26 |
| 16 (Image pickup surface) | ∞ | 0.00 | | |

Various data

| | |
|---|---|
| FNo. | 3.042 |
| ω (half angle of view) | 67.5° |
| IH (mm) | 1 |

EXAMPLE 8

Unit mm

Surface data

| Surface no. | r | d | nd | νd |
|---|---|---|---|---|
| 1 | ∞ | 0.45 | 1.888 | 40.76 |
| 2 | 1.394 | 0.84 | | |
| 3 | −6.786 | 1.00 | 1.972 | 17.47 |
| 4 | −3.645 | 0.64 | | |
| 5 | ∞ | 0.89 | 1.496 | 75.00 |
| 6 (Stop) | ∞ | 0.07 | | |
| 7 | ∞ | 0.31 | | |
| 8 | 60.017 | 1.18 | 1.888 | 40.76 |
| 9 | −3.410 | 0.18 | | |
| 10 | 5.407 | 1.54 | 1.700 | 55.53 |
| 11 | −2.535 | 0.52 | 1.972 | 17.47 |
| 12 | −505.619 | 0.51 | | |
| 13 | 2.011 | 1.64 | 1.518 | 64.14 |
| 14 | ∞ | 0.02 | 1.515 | 64.00 |
| 15 | ∞ | 0.78 | 1.507 | 63.26 |
| 16 (Image pickup surface) | ∞ | 0.00 | | |

Various data

| | |
|---|---|
| FNo. | 2.785 |
| ω (half angle of view) | 69.8° |
| IH (mm) | 1 |

EXAMPLE 9

Unit mm

Surface data

| Surface no. | r | d | nd | νd |
|---|---|---|---|---|
| 1 | ∞ | 0.45 | 1.888 | 40.76 |
| 2 | 1.332 | 1.03 | | |
| 3 | −5.685 | 1.00 | 1.972 | 17.47 |
| 4 | −3.601 | 0.51 | | |
| 5 | ∞ | 0.89 | 1.496 | 75.00 |
| 6 (Stop) | ∞ | 0.07 | | |
| 7 | ∞ | 0.30 | | |
| 8 | 65.092 | 1.15 | 1.888 | 40.76 |
| 9 | −3.201 | 0.41 | | |
| 10 | 4.505 | 1.42 | 1.700 | 55.53 |
| 11 | −2.200 | 0.67 | 1.972 | 17.47 |
| 12 | −33.509 | 0.42 | | |
| 13 | 3.100 | 1.56 | 1.518 | 64.14 |
| 14 | ∞ | 0.02 | 1.515 | 64.00 |
| 15 | ∞ | 0.78 | 1.507 | 63.26 |
| 16 (Image pickup surface) | ∞ | 0.00 | | |

Various data

| | |
|---|---|
| FNo. | 2.963 |
| ω (half angle of view) | 66.0° |
| IH (mm) | 1 |

EXAMPLE 10

Unit mm

Surface data

| Surface no. | r | d | nd | νd |
|---|---|---|---|---|
| 1 | ∞ | 0.45 | 1.888 | 40.76 |
| 2 | 1.297 | 0.95 | | |
| 3 | −4.256 | 0.83 | 1.972 | 17.47 |
| 4 | −3.010 | 0.66 | | |
| 5 | ∞ | 0.89 | 1.496 | 75.00 |
| 6 (Stop) | ∞ | 0.07 | | |
| 7 | ∞ | 0.31 | | |
| 8 | −29.573 | 1.18 | 1.888 | 40.76 |
| 9 | −2.736 | 0.18 | | |
| 10 | 4.823 | 1.64 | 1.700 | 55.53 |
| 11 | −3.010 | 0.83 | 1.972 | 17.47 |
| 12 | 38.674 | 0.51 | | |
| 13 | 2.800 | 1.33 | 1.518 | 64.14 |
| 14 | ∞ | 0.02 | 1.515 | 64.00 |
| 15 | ∞ | 0.78 | 1.507 | 63.26 |
| 16 (Image pickup surface) | ∞ | 0.00 | | |

Various data

| | |
|---|---|
| FNo. | 2.935 |
| Ω (half angle of view) | 66.6° |
| IH (mm) | 1 |

EXAMPLE 11

Unit mm

Surface data

| Surface no. | r | d | nd | νd |
|---|---|---|---|---|
| 1 | ∞ | 0.45 | 1.888 | 40.76 |
| 2 | 1.384 | 0.96 | | |
| 3 | −5.524 | 0.95 | 1.972 | 17.47 |
| 4 | −3.700 | 0.55 | | |
| 5 | ∞ | 0.89 | 1.496 | 75.00 |
| 6 (Stop) | ∞ | 0.07 | | |
| 7 | ∞ | 0.31 | | |
| 8 | −393.692 | 1.18 | 1.888 | 40.76 |
| 9 | −2.987 | 0.18 | | |
| 10 | 5.493 | 1.53 | 1.700 | 55.53 |
| 11 | −2.519 | 0.77 | 1.972 | 17.47 |
| 12 | 2109.790 | 0.51 | | |
| 13 | 2.280 | 1.61 | 1.518 | 64.14 |
| 14 | ∞ | 0.02 | 1.515 | 64.00 |
| 15 | ∞ | 0.78 | 1.507 | 63.26 |
| 16 (Image pickup surface) | ∞ | 0.00 | | |

Various data

| | |
|---|---|
| FNo. | 2.879 |
| ω (half angle of view) | 68.8° |
| IH (mm) | 1 |

EXAMPLE 12

| | Unit mm | | | |
|---|---|---|---|---|
| | Surface data | | | |
| Surface no. | r | d | nd | νd |
| 1 | ∞ | 0.45 | 1.888 | 40.76 |
| 2 | 1.214 | 1.03 | | |
| 3 | −10.910 | 0.97 | 1.972 | 17.47 |
| 4 | −4.120 | 0.23 | | |
| 5 | ∞ | 0.89 | 1.496 | 75.00 |
| 6 (Stop) | ∞ | 0.07 | | |
| 7 | ∞ | 0.32 | | |
| 8 | −3.210 | 0.90 | 1.888 | 40.76 |
| 9 | −2.085 | 0.15 | | |
| 10 | 4.407 | 1.14 | 1.700 | 55.53 |
| 11 | −2.470 | 0.67 | 1.972 | 17.47 |
| 12 | −45.866 | 0.50 | | |
| 13 | 2.785 | 2.89 | 1.518 | 64.14 |
| 14 | ∞ | 0.02 | 1.515 | 64.00 |
| 15 | ∞ | 0.78 | 1.507 | 63.26 |
| 16 (Image pickup surface) | ∞ | 0.00 | | |

| Various data | |
|---|---|
| FNo. | 2.972 |
| ω (half angle of view) | 65.3° |
| IH (mm) | 1 |

The values of conditional expressions in each example are shown below.

| conditional expression |
|---|
| (1) D6/F12 |
| (2) \|F4/F1\| |
| (3) \|F5/F1\| |
| (4) \|(R3R + R4L)/(R3R − R4L)\| |
| (5) F12/R6L |
| (6) R2L/R6L |
| (7) R4R/R3R |
| (8) R4R/R2R |
| (9) \|(R3L + R3R)/(R3L − R3R)\| |
| (10) F45/F6 |

| conditional expression | Example 1 | Example 2 | Example 3 |
|---|---|---|---|
| (1) | −0.596 | −0.627 | −0.477 |
| (2) | 1.734 | 1.610 | 1.699 |
| (3) | 1.718 | 1.604 | 1.708 |
| (4) | 0.282 | 0.235 | 0.253 |
| (5) | −0.860 | −0.802 | −0.741 |
| (6) | −1.849 | −1.920 | −1.516 |
| (7) | 0.866 | 0.796 | 0.885 |
| (8) | 0.680 | 0.600 | 0.691 |
| (9) | 0.989 | 0.801 | 0.980 |
| (10) | 4.064 | 3.818 | 2.708 |

| conditional expression | Example 4 | Example 5 | Example 6 |
|---|---|---|---|
| (1) | −0.566 | −1.188 | −0.676 |
| (2) | 1.543 | 1.772 | 1.862 |
| (3) | 1.634 | 1.985 | 1.984 |
| (4) | 0.168 | 0.299 | 0.497 |
| (5) | −0.889 | −0.857 | −1.084 |
| (6) | −1.877 | −3.586 | −3.973 |
| (7) | 0.735 | 1.179 | 1.194 |
| (8) | 0.630 | 0.600 | 0.605 |
| (9) | 0.949 | 3.357 | 2.134 |
| (10) | 2.317 | 2.315 | 4.081 |

| conditional expression | Example 7 | Example 8 | Example 9 |
|---|---|---|---|
| (1) | −0.550 | −0.544 | −0.576 |
| (2) | 1.677 | 1.707 | 1.542 |
| (3) | 1.705 | 1.671 | 1.632 |
| (4) | 0.229 | 0.226 | 0.169 |
| (5) | −0.624 | −1.499 | −0.874 |
| (6) | −1.538 | −3.374 | −1.834 |
| (7) | 0.813 | 0.743 | 0.687 |
| (8) | 0.600 | 0.695 | 0.611 |
| (9) | 0.881 | 0.892 | 0.906 |
| (10) | 2.300 | 7.071 | 2.303 |

| conditional expression | Example 10 | Example 11 | Example 12 |
|---|---|---|---|
| (1) | −0.511 | −0.619 | −1.072 |
| (2) | 1.984 | 1.718 | 1.775 |
| (3) | 1.948 | 1.661 | 1.980 |
| (4) | 0.276 | 0.296 | 0.358 |
| (5) | −0.929 | −1.141 | −0.968 |
| (6) | −1.520 | −2.423 | −3.917 |
| (7) | 1.100 | 0.843 | 1.185 |
| (8) | 1.000 | 0.681 | 0.600 |
| (9) | 1.204 | 1.015 | 4.706 |
| (10) | 3.976 | 7.227 | 2.356 |

The aforementioned endoscope objective optical system may satisfy a plurality of arrangements simultaneously. Making such arrangement is preferable for achieving a favorable endoscope objective optical system. Moreover, combinations of preferable arrangements are voluntary. Furthermore, regarding each conditional expression, only an upper limit value or a lower limit value of a numerical range of a further restricted conditional expression may be restricted.

The embodiments and various examples of the present invention are described above. However, the present invention is not restricted to these embodiments and examples, and embodiments formed by combining arrangement of these embodiments and examples without departing from the scope of the present invention are also included in the category of the present invention.

The present embodiment shows an effect that it is possible to provide a high-performance endoscope objective optical system which is small-sized and is capable of securing an adequate observation depth, and which has a wide angle of view, and which makes easy an observation and diagnosis of a pathological lesion.

As described heretofore, the present invention is useful for a high-performance endoscope objective optical system which is small-sized and is capable of securing an adequate observation depth, and which has a wide angle of view, and which makes easy an observation and diagnosis of a pathological lesion.

What is claimed is:

1. An endoscope objective optical system comprising, in order from an object side:
   a front group having a negative refractive power as a whole;
   an aperture stop; and
   a rear group having a positive refractive power as a whole, wherein:
   the front group consists of a first lens which is a single lens having a negative refractive power, and a second lens which is a single lens having a positive refractive power, in order from the object side, the rear group consists of a third lens which is a single lens having a positive refractive power, a cemented lens of a fourth lens having a positive refractive power and a fifth lens having a negative refractive power, and a sixth lens having a positive refractive power, an object-side surface of the first lens is a flat surface, the second lens has a meniscus shape with a convex surface directed toward an image side, the sixth lens is cemented to an image pickup element, the following conditional expression (1) is satisfied:

$$-1.2 \leq D6/F12 \leq -0.47 \quad (1)$$

where,

D6 denotes a thickness of the sixth lens, and

F12 denotes a combined focal length from the first lens up to the second lens, and the following conditional expression (9) is satisfied:

$$0.5 \leq |(R3L+R3R)/(R3L-R3R)| \leq 5 \quad (9)$$

where,

R3R denotes a radius of curvature of an image side of the third lens, and

R3L denotes a radius of curvature of an object side of the third lens.

2. The endoscope objective optical system according to claim 1, wherein the following conditional expression (2) is satisfied:

$$1.5 \leq |F4/F1| \leq 2.0 \quad (2)$$

where,

F4 denotes a focal length of the fourth lens, and

F1 denotes a focal length of the first lens.

3. The endoscope objective optical system according to claim 1, wherein the following conditional expression (3) is satisfied:

$$1.6 \leq |F5/F1| \leq 2.0 \quad (3)$$

where,

F5 denotes a focal length of the fifth lens, and

F1 denotes a focal length of the first lens.

4. The endoscope objective optical system according to claim 1, wherein the following conditional expression (4) is satisfied:

$$0.16 \leq |(R3R+R4L)/(R3-R\ R4L)| \leq 0.5 \quad (4)$$

where,

R3R denotes the radius of curvature of the image side of the third lens, and

R4L denotes a radius of curvature of an object side of the fourth lens.

5. The endoscope objective optical system according to claim 1, wherein the following conditional expressions (5) and (6) are satisfied:

$$-2.0 \leq F12/R6L \leq -0.62 \quad (5)$$

$$-4.0 \leq R2L/R6L \leq -1.5 \quad (6)$$

where,

F12 denotes the combined focal length from the first lens up to the second lens, R6L denotes a radius of curvature of an object side of the sixth lens, and R2L denotes a radius of curvature of an object side of the second lens.

6. The endoscope objective optical system according to claim 1, wherein the following conditional expression (7) is satisfied:

$$0.55 \leq R4R/R3R \leq 1.2 \quad (7)$$

where,

R4R denotes a radius of curvature of an image side of the fourth lens, and

R3R denotes the radius of curvature of the image side of the third lens.

7. The endoscope objective optical system according to claim 1, wherein the following conditional expression (8) is satisfied:

$$0.6 \leq R4R/R2R \leq 1.0 \quad (8)$$

where,

R4R denotes a radius of curvature of an image side of the fourth lens, and

R2R denotes a radius of curvature of an image side of the second lens.

8. The endoscope objective optical system according to claim 1, wherein the following conditional expression (10) is satisfied:

$$2.3 \leq F45/F6 \leq 7.3 \quad (10)$$

where,

F45 denotes a focal length of the cemented lens of the fourth lens and the fifth lens, and F6 denotes a focal length of the sixth lens.

9. An endoscope comprising:

the endoscope objective optical system according to claim 1.

10. An image pick-up apparatus comprising:

the endoscope objective optical system according to claim 1; and an imager.

* * * * *